United States Patent [19]

Kleinberg et al.

[11] Patent Number: 5,023,551
[45] Date of Patent: Jun. 11, 1991

[54] NUCLEAR MAGNETIC RESONANCE PULSE SEQUENCES FOR USE WITH BOREHOLE LOGGING TOOLS

[75] Inventors: Robert L. Kleinberg, Ridgefield; Abdurrahman Sezginer, Brookfield, both of Conn.; Masafumi Fukuhara, Sagamihara, Japan

[73] Assignee: Schlumberger-Doll Research, New York, N.Y.

[21] Appl. No.: 452,903

[22] Filed: Dec. 19, 1989

Related U.S. Application Data

[63] Continuation-in-part of Ser. No. 368,916, Jun. 19, 1989, Pat. No. 4,933,638, which is a continuation of Ser. No. 901,084, Aug. 27, 1986, abandoned.

[51] Int. Cl.$^5$ ............................................. G01R 33/20
[52] U.S. Cl. ...................................... 324/303; 324/307
[58] Field of Search ............... 324/300, 303, 307, 309, 324/310, 311, 312, 313, 314, 318, 322; 128/653 A

[56] References Cited

U.S. PATENT DOCUMENTS

| | | |
|---|---|---|
| 3,226,632 | 4/1962 | Brown et al. . |
| 3,597,681 | 8/1971 | Hackabay ............................ 324/303 |
| 3,781,650 | 12/1973 | Keller . |
| 4,297,637 | 10/1981 | Crooks et al. . |
| 4,389,613 | 6/1983 | Brown .................................. 324/312 |
| 4,408,161 | 10/1983 | Brown .................................. 324/307 |
| 4,431,968 | 2/1984 | Edelstein et al. . |
| 4,443,760 | 4/1984 | Edelstein et al. . |

(List continued on next page.)

OTHER PUBLICATIONS

Freeman and Hill, Fourier Transformation Study of NMR Spin Lattice Relaxation by "Progressive Saturation", Journal of Chemical Physics, vol. 54, No. 8, Apr. 15, 1971; pp. 3367-3377.

(List continued on next page.)

Primary Examiner—Michael J. Tokar
Attorney, Agent, or Firm—David P. Gordon; Peter Y. Lee

[57] ABSTRACT

An NMR pulse sequence for use in the borehole environment is provided which combines a modified fast inversion recovery (FIR) pulse sequence with a series of more than ten, and typically hundreds, of CPMG pulses according to $$[W_i-180-\tau_i-90-(t_{cp}-180-t_{cp}-\text{echo})_j]_i$$

where j is the index of the CPMG echoes gathered, i is the index of the wait times in the pulse sequence, $W_i$ are the wait times, i are the recovery times before the CPMG pulses, and tcp is the Carr-Purcell spacing. Measurements are made of the signals induced in the formation as a result of the magnetic fields. Determinations of $M_o$ and/or T1 are then made from the measurements according to relationships which relate $Mp_o$, T1 and T2 to the signal magnitude. Other relationships which provide stretched exponentials or multiple exponentials can also be used. From the $M_o$ and/or T1 determinations, formation parameters such as porosity and permeability may be derived according to equations known in the art. In obtaining the most accurate determinations of formation parameters in the least amount of time, the various pulse sequence parameters (I, J, $W_i$, and $\tau_i$) are optimized prior to logging. Additional accuracy is obtained by integrating a gated portion of the echoes rather than by measuring amplitude, and by utilizing a phase alternated CPMG sequence in repetitive measurements in order to eliminate baseline shift error.

62 Claims, 5 Drawing Sheets

U.S. PATENT DOCUMENTS

| | | |
|---|---|---|
| 4,451,788 | 5/1984 | Edelstein et al. . |
| 4,459,139 | 10/1985 | MacFall et al. . |
| 4,471,305 | 9/1984 | Crooks et al. . |
| 4,471,306 | 9/1984 | Edelstein et al. . |
| 4,480,227 | 10/1984 | Brown .................... 324/303 |
| 4,486,709 | 12/1984 | Bendall . |
| 4,521,733 | 6/1985 | Bottomley et al. . |
| 4,536,712 | 8/1985 | Iwaoka et al. . |
| 4,542,343 | 9/1985 | Brown .................... 324/307 |
| 4,570,119 | 2/1986 | Wehrli et al. . |
| 4,570,120 | 2/1986 | Hall et al. . |
| 4,579,121 | 4/1986 | Macovski . |
| 4,604,579 | 8/1986 | Cannon . |
| 4,612,504 | 9/1986 | Pelc . |
| 4,616,183 | 10/1986 | Glover et al. . |
| 4,620,154 | 10/1986 | Inouye . |
| 4,621,235 | 11/1986 | van Uijen et al. . |
| 4,628,262 | 12/1986 | Maudsley . |
| 4,641,095 | 2/1987 | Riederer . |
| 4,651,097 | 3/1987 | Iwaoka et al. . |
| 4,656,425 | 4/1987 | Bendel . |
| 4,665,367 | 5/1987 | Kramer et al. . |
| 4,684,891 | 8/1987 | Feinberg . |
| 4,684,892 | 8/1987 | Graumann . |
| 4,697,148 | 9/1987 | Strobel et al. . |
| 4,698,593 | 10/1987 | Crooks . |
| 4,701,709 | 10/1987 | Yamamoto et al. . |
| 4,707,658 | 11/1987 | Frahm et al. . |
| 4,709,211 | 11/1987 | Machida et al. . |
| 4,709,212 | 11/1987 | MacFall et al. . |
| 4,710,713 | 12/1987 | Strikman .................... 324/303 |
| 4,710,718 | 12/1987 | Shaka . |
| 4,717,877 | 1/1988 | Taicher et al. . |
| 4,719,423 | 1/1988 | Vinegar et al. . |

OTHER PUBLICATIONS

Levy and Peat; The Experimental Approach to Accurate Carbon-13 Spin-Lattice Relaxation Measurements; Jour. of Magnetic Resonance 18, pp. 500–521; 1975.

Meakin and Jesson; Computer Simulation of Multiphase & Fourier Transform NMR Experiments . . . ; Jour. of Magnetic Resonance 10; pp. 290–315; 1973.

Allerhand and Cochran; Carbon-13 Fourier-Transform Nuclear Magnetic Resonance . . . ; Jour. of the Amer. Chemical Society; Jul. 15, 1970; 94:14.

J. S. Waugh; Sensitivity in Fourier Transform NMR Spectroscopy of Slowly Relaxing Systems; Jour. of Molecular Spectroscopy 35; 1970, pp. 298–305.

Meiboom and Gill; Modified Spin-Echo Method for Measuring Nuclear Relaxation Times; The Review of Scientific Instruments; vol. 29, No. 8, Aug. 1958.

Carr and Purcell; Effects of Diffusion on Free Precession in Nuclear Magnetic Resonance Experiments; Physical Review, vol. 94, No. 3.

H. Edzes; An Analysis of the Use of Pulse Multiplets in the Single Scan Determination . . . ; Jour. of Magnetic Resonance 17, pp. 301–313; 1975.

Canet, Levy and Peat; Time Saving in C Spin-Lattice Relaxation Measurements by Inversion-Recovery; Jour. of Magnetic Resonance 18; pp. 199–204; 1975.

POROSITY (ROCK LAB)

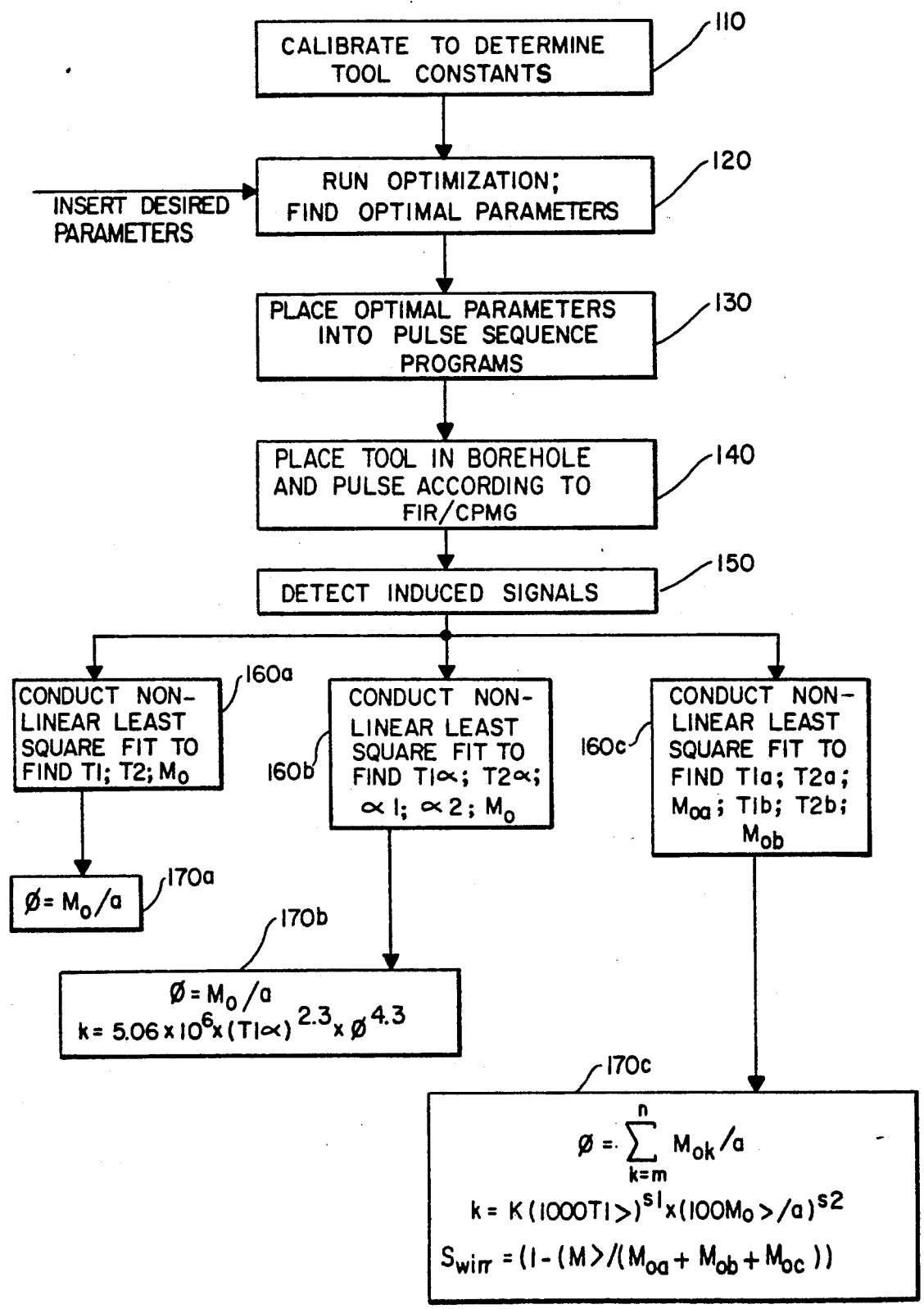

NUCLEAR MAGNETIC RESONANCE PULSE SEQUENCES FOR USE WITH BOREHOLE LOGGING TOOLS

This is a continuation-in-part of copending SN 07/368,916 filed June 19, 1989, now U.S. Pat. No. 4,933,638 which is a continuation of SN 06/901,084, filed on Aug. 27, 1986 and now abandoned, and assigned to the assignee hereof, which is hereby incorporated by reference herein.

BACKGROUND

1. Field of the Invention

This invention generally relates to nuclear magnetic resonance (NMR) pulse sequences useful in the evaluation of earth formations. More particularly, the invention relates to NMR pulse sequences which may be used by a nuclear magnetic resonance logging tool for measuring earth formation properties such as porosity, permeability, and irreducible water saturation.

2. Prior Art

Nuclear magnetic logging tools such as disclosed in parent patent application SN 06/901,084, measure the number and nuclear magnetic relaxation rates of hydrogen atoms in the pore space of rocks by measuring the amplitude and decay rate of signals resulting from pulse sequences. In essence, the nuclear magnetic logging tools send a stream of pulses into the formation and monitor the returning pulses. The measurements made are typically cyclical, with each cycle taking several seconds. Interpretation algorithms are then used to find the formation properties of interest.

Measurable Formation Properties

The strength of the nuclear magnetic signal is directly proportional to the number of resonated spins present in the probed volume. Because hydrogen is the nucleus of choice in most borehole measurements, and because NMR tools can be tuned in frequency to resonate a particular nuclear species, the signal amplitude of a tuned tool measures the number of hydrogen atoms in the formation. The number of hydrogen atoms in the formation in turn is related to fluid filled porosity. In addition to being sensitive to hydrogen density, nuclear magnetism tools are sensitive to the environment of the hydrogen being probed. As shown in FIG. 1, hydrogen in a bound or "irreducible" fluid typically has a spin-lattice relaxation time (T1) in the milliseconds to tens of milliseconds, while free or producible fluid has a T1 in the range of tens to hundreds of milliseconds. Hydrogen in a solid matrix has a long T1, (several seconds or longer), but because it is measured via T2 measurements in the hereinafter described invention, and because hydrogen in a solid matrix has a very short T2 spin-spin relaxation time which is invisible to measurement tools, the hydrogen in the solid matrix is invisible to the measurement tool. Fortuitously, then, in the hereinafter described invention, the decaying NMR signals received by the nuclear magnetic tools are not corrupted by the hydrogen in the matrix, as no known borehole nuclear magnetic logging tool has a short enough deadtime to detect a spin-spin relaxation time signal from the matrix. Rather, the NMR tools are able to detect all fluid protons which are indicative of the fluid filled porosity of the formation. FIG. 2 illustrates the results of a total porosity measurement of twenty-three water-filled cores from oil fields all over the world. The horizontal axis is the bouyancy porosity as measured in a laboratory. The vertical axis is the porosity as determined by a laboratory prototype NMR tool using a pulse sequence as described hereinbelow.

Besides correlating well to porosity, the measurements resulting from the NMR sequences applied to the formation provide information which may be correlated with the "free fluid index", permeability, and residual oil saturation. The concept of "free fluid index" is largely based on work by Seevers, "A Nuclear Magnetic Method for Determining the Permeability of Sandstones", *7th SPWLA Logging Symp.*, (1966, Paper L), and Timur, "Pulsed Nuclear Magnetic Resonance Studies of Porosity, Movable Fluid, and Permeability of Sandstones", *Journal of Petroleum Technology*, (June 1969, pp. 775-786). Timur successfully correlated the amplitude of slowly decaying components of spin-lattice (T1) relaxation curves with the quantity of fluid movable by centrifugation. Timur decomposed the spin-lattice relaxation curves into three exponentially decaying components:

$$V(t) = A\exp(-t/T1_A) + B\exp(-t/T1_B) + C\exp(-t/T1_C) \quad (1)$$

Timur found an excellent correlation between movable fluid and the summed amplitudes of all components having relaxation times greater than twelve milliseconds.

A number of transforms have been introduced to determine permeability by well logs. A major advance in permeability logging was disclosed by Kenyon, W. et al. "SPE Formation Evaluation", Sept. 1988 (pg. 622-636), where evidence of a correlation between NMR relaxation time (T1) and permeability was presented for water filled sandstones.

Residual oil saturation may only be determined by eliminating the signal contributed by the water phase of the permeable formation. The same is accomplished by introducing paramagnetic ions which are soluble only in the water phase and which decrease the relaxation time of the hydrogen in water to below the level of observability. Resulting amplitude measurements in the borehole therefore provide a measurement of only the oil phase. Tools Available in Art for Making NMR Measurements Downhole Borehole tools for accomplishing the measurements required for a determination of porosity, permeability, residual oil saturation, etc. impose many special conditions on nuclear magnetic measurements. Proposals for overcoming the difficulties were presented as early as 1960, by Brown and Gamson, "Petroleum Transactions of the AIME," 219, 199 (1960), which resulted in a "Nuclear Magnetism Tool" which was subsequently commercialized by the assignee hereof. The Nuclear Magnetism Tool comprises a large coil to which direct current is applied. The resulting static field polarizes nuclear spins in a region approximately one foot in radius centered on the mandrel on which the coil is mounted. The current is then switched off, and the nuclear spins in the polarized region precess in the earth's magnetic field, inducing a voltage in the coil. The proton signal is selected using a bandpass filter. The length of time the direct current is passed through the coil before being turned off is systematically varied. By correlating the amplitude of the received voltage with the length of time the direct current is left on immediately prior to the measurement, the nuclear magnetic resonance properties of the earth material of the formation can be determined. With the Nuclear Magnetism Tool, no pulses of oscillating fields are used.

Because of difficulties inherent in the measurement process, and inaccuracies in provided results of the Nuclear Magnetism Tool, new tools have been developed over the last ten years. Among these tools are those disclosed in U.S. Pat. No. 4,350,955 to Jackson et al., U.S. Pat. No. 4,710,713 to Strikman, and copending parent application SN 06/901,084 to Kleinberg et al. These new tools, which are substantially different in hardware configuration from the Nuclear Magnetism Tool and from each other, have in common the necessity of using pulses of an oscillating magnetic field for manipulating the nuclear spins of the earth formation. The new tools also have in common the fact that they utilize pulse NMR techniques developed in the chemical physics community to measure the NMR parameters of materials. Peculiarities of Borehole NMR Logging In designing a downhole tool utilizing NMR properties, it is important to recognize that there are several requirements beyond those of NMR measurements made in other settings. The additional requirements arise because of the peculiarities of the borehole setting: i.e. the NMR properties of rocks are unlike the NMR properties of other materials; the borehole apparatus is unlike any other kind of apparatus; logging of NMR properties might occur during movement of the borehole tool past heterogeneous bodies; various different measurements such as T1 and T2 relaxations are both desirable and must be made simultaneously and extremely quickly; and accuracy in quantitative measurements (as opposed to relative values) is critical.

It is presently standard in the art to assume that the spin-lattice (T1) and spin-spin (T2) relaxations of the nuclear magnetism of most materials are described by single exponential decay laws. Indeed, in most material science investigations conducted in academic and industrial laboratories, the two quantities T1 and T2 are usually considered together with an amplitude determination to completely describe the NMR properties of the materials under investigation However, the inventors have found in investigating rock properties that a single exponential decay is inadequate to describe T1 and T2, and that attempting to do so can produce misleading results. For example, as shown by Kenyon et al. "SPE Formation Evaluation", September 1988 (pg 622–636), the correlation between permeability and NMR T1 is only valid when the "stretched exponential" decay constant $T1\alpha$ is used. Similarly, the permeability correlation of Timur in Timur, "Pulsed Nuclear Magnetic Resonance Studies of Porosity, Movable Fluid, and Permeability of Sandstones", *Journal of Petroleum Technology*, (June 1969 pg 775–786), depends explicitly on the measurement of a multi-exponential decay curve. Thus, the use of a single exponential analysis of rock data will give an incorrect value for permeability. A single exponential analysis of rock NMR data also obscures some of the most important petrophysical information that can be derived from the measurement. Viewed as a multi-exponential decay curve, rock NMR data can be used to quantitatively measure the amounts of immovable fluid (fast relaxing component) and movable fluid (slow relaxing component). The latter is of tremendous importance in the evaluation of oil reservoirs, as it is only the movable fluid that can be produced from a well. The stretched exponential analysis can also be used to distinguish movable from immovable fluid. Moreover, the value of the stretch exponent $\alpha$ contains information on pore size distribution of the rock. Such information is desired in the oil industry. Hence, any pulse sequence to be used to characterize rock NMR properties should take into account the stretched exponential or multiple exponential nature of the magnetization decays.

As aforementioned, the borehole tool is inherently restrictive by nature. The requirement of making NMR measurements in situ places significant and unusual demands on the instrument designer. For example, instrument dead time, which is considered a minor detail by NMR practitioners outside of the borehole, is of considerable significance inside the borehole. In particular, nuclear magnetic resonance apparatus used in laboratories or similar settings comprise large electromagnets or current carrying coils inside which the sample to be investigated is placed. This allows large static fields to be used. According to the Larmor condition, the operating frequency of the spectrometer is proportionately high. As is known to those skilled in the borehole arts, high frequency electronics recover much more rapidly from overload than low frequency electronics. In practice, it is found that borehole NMR instruments operate at a frequency of the order of 1 MHZ. It takes about fifty microseconds for a 1 MHz system to recover from a several hundred volt pulse and be ready to receive a submicrovolt signal. In order for the NMR spectrometer to measure a free induction decay (FID), as is the typical practice in all but borehole NMR spectrometers, the dead time must be shorter than the decay time constant of the FID. This decay time constant is conventionally termed $T2^*$. $T2^*$ is controlled by the inhomogeneity of the static magnetic field Bo. If Bo is homogeneous, $T2^*$ is long, and conversely, if Bo Is inhomogeneous, $T2^*$ is short. Because borehole NMR tools must project the static field to a region well outside the housing in which the magnets are contained, the magnetic fields are inevitably less homogeneous than those found in NMR laboratories, and so $T2^*$ is shorter. For example, for the tool disclosed in copending SN 07/368,916, $T2^*$ is approximately thirty-five microseconds. Because dead times of up to fifty microseconds are common in borehole NMR device, it becomes apparent that FIDs are not observable by borehole NMR devices, and any pulse sequence utilizing FIDs will not be effective in the borehole arts. Since many pulse sequences of the prior art do in fact use FID information, the limitations inherent in borehole tools are seen to provide significant limitations and disadvantages.

Another peculiarity of the borehole situation is that the apparatus which both induces and measures a signal in the formation is typically moving past the formation sample at a non-negligible rate of speed during the logging process. Because earth formations are inhomogeneous, and frequently contain "fining upwards" or "coarsening upwards" sequences in which gradients of NMR properties exist, the NMR sequence utilized by the tool must help minimize undesirable effects arising from the traversal of heterogeneous formations.

As opposed to the medical arts where a qualitative measurements of T1 and T2 provide contrasts suitable for imaging, in the borehole arts, extremely accurate quantitative measurements of T1 and T2 are desired. Such accurate measurements are required because the porosity and free fluid index of the formation are proportional to the signal amplitude, and should be measured to within one porosity unit to be considered useful by the oil industry. Similarly, because permeability should be measured to within a factor of three to be useful, the stretch exponential spin-lattice relaxation time T1, must be measured to within twenty percent (as disclosed by Kenyon et al.). Of course, the accurate measurements should be obtained in the shortest amount of time because of the great expense associated with operating oil well drilling equipment, as well as risk of the borehole collapsing before it is cased. Therefore, it is a practical necessity that all NMR measurements be made and are collected as rapidly as possible.

Principles of NMR and Sequences Used in the Art

NMR has been a common laboratory technique for forty years, and a complete, exact theoretical description is available in Abragam, *Principles of Nuclear Magnetism,* Clarendon Press (Oxford, 1961), and Farrar and Becker, *Pulse and Fourier Transform NMR,* Academic Press (New York 1971). NMR is based on the fact that the nuclei of many elements have angular momentum ("spin") and a magnetic moment. The nuclear spins align themselves along an externally applied static magnetic field. This equilibrium situation can be disturbed by a pulse of an oscillating magnetic field, which tips the spins away from the static field direction The angle through which the spins are tipped is under the control of the experimenter, as explained below.

After tipping, two things occur simultaneously. First, the spins precess around the static field at a particular frequency (i.e. the Larmor frequency), given by $\omega_0 = \gamma B_o$, where $B_o$ is the strength of the static field and $\gamma$ is the gyromagnetic ratio, a nuclear constant. Second, the spins return to the equilibrium direction according to a decay time known as the "spin-lattice relaxation time" or T1. For hydrogen nuclei, $\gamma/2\pi = 4258$ Hz/Gauss. So for a static field of 235 Gauss, the frequency of precession is 1 MHz. T1 is controlled totally by the molecular environment and is typically ten to one thousand milliseconds in rocks. Each spin can be thought of as moving back toward equilibrium in a very tight pitch spiral during the T1 decay.

Also associated with the spin of molecular nuclei is a second relaxation time known as the "spin-spin relaxation time" or T2. At the end of a ninety degree tipping pulse, all the spins are pointed in a common direction perpendicular to the static field, and they all precess at the Larmor frequency. However, because of small inhomogeneities in the static field due to imperfect instrumentation or microscopic material heterogeneities, each nuclear spin precesses at a slightly different rate. Hence, after a time long compared to the precession period, but shorter than T1, the spins will no longer be precessing in unison. When this dephasing is due to static field inhomogeneity of the apparatus, the dephasing is called T2*. When it is due to properties of the material, the dephasing time is called T2. T2 and T2* can be measured independently as hereinafter described. For rocks, T2 is approximately one-half of T1.

As aforementioned, the parameters T1 and T2 are sensitive to molecular environment. For example, T2 can be several seconds in an unconfined low viscosity liquid such as water, while it can be as short as ten microseconds in a solid. As aforementioned, liquids confined in the pores of rocks present an intermediate case with T2 in the range of tens to hundreds of milliseconds, depending on pore size and fluid viscosity.

In the basic NMR measurement, a pulse of oscillating field is applied to the sample to tip the spins of the nuclei in the sample. The angle (in radians) through which the spins are tipped is given by the equation $$\theta = \gamma B_1 t_p/2 \qquad (2)$$

where $\gamma$ is the gyromagnetic ratio, $B_1$ is the linearly polarized oscillating field strength, and $t_p$ is the duration of the pulse. Tipping pulses of ninety and one hundred and eighty degrees are the most common.

The precessing spins are detected by voltage induced in a coil. Only that component of the nuclear magnetization that is precessing in the plane perpendicular to the static field can be sensed by the coil. Hence, a signal will be generated after a ninety degree tipping pulse but not after a one hundred eighty degree tipping pulse. In fact, after a one hundred eighty degree tipping pulse, the spins do not precess at all, but just slowly return along the $B_o$ axis to the equilibrium direction.

In measuring the spin-lattice relaxation time T1, many different techniques are known both in the material science arts and in the medical arts. The "inversion recovery" technique suggests that after the nuclei have aligned themselves along the static magnetic field, a one hundred eighty degree pulse is applied to reverse the direction of the spins. Over time, the spins decay toward their equilibrium direction according to T1, but no measurement is yet made as the one hundred eighty degree pulse does not induce a signal in the coil. Before the decay is complete, however, it is interrupted by a ninety degree pulse which rotates the spins into the measurement plane (i.e. induces a signal in the coil). However, the measurable signal lasts only as long as the spins precess in unison. As they dephase, the net magnetization decreases, even if all the spins remain in the transverse plane. Therefore, the signal decays exponentially with time constant T2*, also known as the "free induction decay". Fortunately, the information of interest is the amplitude of the signal immediately after the ninety degree "read out" pulse. This amplitude clearly depends on the "recovery time" ($\tau$) between the original one hundred eighty degree pulse and the ninety degree pulse. Following a determination of amplitude, the spin system is permitted to completely relax back to equilibrium, and the pulse sequence is then repeated preferably numerous times with different recovery times. The detected amplitudes are then plotted against $\tau$ with the decay typically being expressed as a single exponential.

The inversion recovery technique for measuring T1 has been used in laboratories for almost thirty-five years. It is very time consuming, and therefore undesirable for well logging and other material property investigations. To overcome some of the shortcomings of inversion recovery, other techniques such as preparation recovery, steady state, and magnetization conserving techniques have been developed.

The preparation recovery techniques are generally straightforward improvements on the inversion recovery method, and generally recognize that it is not necessary to wait for the spin system to return to equilibrium between measurement cycles. All that is essential, is that the state of the spin system at the start of the recovery period be known. In the "saturation recovery" technique, the spin system is saturated with several ninety degree pulses which reduce the magnetization to zero. The spin system is then allowed to recover for a variable length of time prior to applying a monitor pulse. The "fast inversion recovery technique" allows some relaxation of the spin system toward equilibrium between pulse cycles, but does not wait until complete relaxation is obtained. Other preparation recovery modifications are also known in the art.

A second major class of spin-lattice relaxation measurements is the steady state or "progressive saturation" methods. In progressive saturation, the perturbations produced by a long train of equally spaced ninety degree pulses are in dynamic balance with the relaxation toward equilibrium. T1 is then determined by varying the time between pulses and measuring the steady state signal. Modifications of the progressive saturation method are to use pulses that are not ninety degrees, or to vary the tip angle of the perturbing pulses while keeping the recovery time constant.

Magnetization conserving methods are a third major class of techniques. They are based on the removal of magnetization from the measurement plane before it is destroyed by T2 processes. The magnetization conserving methods are often called z-restored spin echo or triplet pulse sequences. In an exemplary technique, the spin system is inverted with a one hundred eighty degree pulse, the relaxation along the longitudinal direction is monitored by rotating the magnetization into the transverse plane, and then the spins are rotated back to the longitudinal direction for continued relaxation. Several plus and minus ninety degree rotations may occur during a single relaxation to provide several data points.

Comparisons between various of the known methods have been made (See, e.g. Levy and Peat, "The Experimental Approach to Accurate Carbon-13 Spin-Lattice Relaxation Measurements", *Journal of Magnetic Resonance* 18, (1975 pp. 500–521), and Becker et al. "The Choice of Optimal Parameters for Measurement of Spin-Lattice Relaxation Times. II. Comparison of Saturation Recovery, Inversion Recovery, and Fast Inversion Recovery Experiments", *Journal of Magnetic Resonance* 37 (1980 pp. 381–394). In fact, Becker et al. have partially optimized and compared the inversion recovery, saturation recovery, and fast inversion recovery methods and found that the fast inversion recovery technique, with a waiting time equal to twice the longest expected T1 is superior to the other two techniques.

While many different methods for measuring T1 have been developed, a single standard known as the CPMG sequence (Carr-Purcell-Meiboom-Gill) for measuring T2 has evolved. In solids, where T2 is very short, T2 can be determined from the decay of liquids where $T2^* << T2$, the free induction decay becomes a measurement of the apparatus-induced inhomogeneities. To measure the true T2 in such situations, it is necessary to cancel the effect of the apparatus-induced inhomogeneities. To accomplish the same, a series of pulses is applied. First a ninety degree pulse causes the spins to start precessing. Then a one hundred eighty degree pulse is applied to keep the spins in the measurement plane, but to cause the spins which are dispersing in the tranverse plane to reverse direction and to refocus. By repeatedly reversing the spins by one hundred eighty degree pulses, a series of "spin echoes" appear as seen in FIG. 3. This succession of one hundred eighty degree pulses after an initial ninety degree pulse is the Carr-Purcell sequence which measures the irreversible dephasing (i.e. T2) due to material properties.

While the Carr-Purcell sequence would appear to provide a solution to eliminating apparatus induced inhomogeneities, it was found by Meiboom and Gill that if the one hundred eighty degree pulses in the Carr-Purcell sequence were slightly misset, the tranverse magnetization would steadily be rotated out of the tranverse plane. As a result, substantial errors would enter the T2 determination. Thus, Meiboom and Gill devised a modification to the Carr-Purcell pulse sequence such that after the spins are tipped by ninety degrees and start to dephase, the carrier of the one hundred eighty degree pulses is phase shifted relative to the carrier of the ninety degree pulse. As a result, any error that occurs during an even pulse of the CPMG sequence is cancelled out by an opposing error in the odd pulse.

The pulse sequences used in the materials science arts for determination of T1 and T2 as aforedescribed, are relatively easily listed and categorized. On the other hand, in the non-analogous NMR medical arts, where imaging is paramount, quantitative measurement is often secondary, and the measurement environment poses fewer problems, numerous pulse sequences have been proposed. Representative of U.S. Patents in the NMR (almost exclusively medical) arts are as follows:

| U.S. Pat. No. | Inventor | U.S. Pat. No. | Inventor |
| --- | --- | --- | --- |
| 3,226,632 | Brown | 3,781,650 | Keller |
| 4,297,637 | Crooks et al. | 4,408,161 | Brown |
| 4,431,968 | Edelstein et al | 4,443,760 | Edelstein et al |
| 4,486,709 | Bendall | 4,451,788 | Edelstein et al |
| 4,471,305 | Crooks | 4,471,306 | Edelstein et al |
| 4,521,733 | Bottomley et al. | 4,536,712 | Iwaoka et al. |
| 4,549,139 | MacFall et al. | 4,570,119 | Wehrli et al. |
| 4,570,120 | Hall et al. | 4,579,121 | Macovski |
| 4,604,579 | Cannon et al. | 4,612,504 | Pelc |
| 4,616,183 | Glover et al. | 4,620,154 | Inouye |
| 4,621,235 | van Uijen et al | 4,628,262 | Maudsley |
| 4,641,095 | Riederer | 4,651,097 | Iwaoka et al. |
| 4,665,367 | Kramer et al. | 4,656,425 | Bendel |
| 4,684,891 | Feinberg | 4,684,892 | Gruamann |
| 4,697,148 | Stobel et al. | 4,698,593 | Crooks |
| 4,701,709 | Yamamoto et al. | 4,707,658 | Frahm et al. |
| 4,709,211 | Machida et al. | 4,709,212 | MacFall et al. |
| 4,710,718 | Shaka | 4,717,877 | Taicher et al. |
| 4,718,423 | Vinegar et al. | | |

Representative articles in the material sciences arts are: Carr & Purcell, "Effects of Diffusion on Free Precession in Nuclear Magnetic Resonance Experiments", *Physical Review*, Vol. 94, No. 3 May 1, 1954).

Meiboom & Gill, "Modified Spin-Echo Method for Measuring Nuclear Relaxation Times", *The Review of Scientific Instruments*, Vol 29, No. 8 Aug. 1958).

Waugh, "Sensitivity in Fourier Transform NMR Spectroscopys of Slowing Relaxing Systems", *Journal of Molecular Spectroscopy* 35, (pp. 298–305 1970).

Allerhand & Cochran, "Carbon-13 Fourier-Transform Nuclear Magnetic Resonance. I. Comparison of Simple Spin-Echo Procedure With Other Methods", *Journal of the American Chemical Society* 92:14, July 15, 1970.

Freeman & Hill, "Fourier Transform Study of NMR Spin-Lattice Relaxation by "Progressive Saturation"", *The Journal of Chemical Physics*, Vol. 54, No. 8 (pp. 3367–3377, 4/15/71).

Meakin & Jesson, "Computer Simulation of Multipulse and Fourier Transform NMR Experiments. I. Simulations Using the Bloch Equations", *Journal of Magnetic Resonance* 10, (pp. 290–315 (1973).

Edzes, "An Analysis of the Use of Pulse Multiplets in the Single Scan Determination of Spin-Lattice Relaxation Rates", *Journal of Magnetic Resonance* 17, (pp. 301–315 (1975).

Canet, et al., "Time Saving in 13C Spin-Lattice Relaxation Measurements by Inversion-Recovery", *Journal of Magnetic Resonance* 18, (pp. 199–204, 1975).

Levy & Peat, "The Experimental Approach to Accurate Carbon-13 Spin-Lattice Relaxation Measurements", *Journal of Magnetic Resonance* 18, (pp. 500–521, 1975).

Several matters of interest relate to the above-listed documents. First, the documents are by no means an exhaustive list of available art. In fact, a review of the references cited in the patents and articles themselves will provide additional lists of relevant documents. Second, it will be seen in the review of the above-listed documents as well as other available documents that there is at most minimal cross-over between the medical and material science arts regarding NMR pulse sequences. Perhaps this lack of cross-over is a function of the fact that the requirements of the medical and material science investigations are so substantially different, particularly where the borehole is concerned. A third matter of interest is that the Bendel U.S. Pat. No. 4,656,425 and Graumann U.S. Pat. No. 4,684,892 both disclose a pulse sequence (in FIGS. 2B and 2 respectively) for use in medical imaging which is similar in several ways to the preferred embodiment of the instant invention which is disclosed in detail below.

SUMMARY OF THE INVENTION

It is therefore an object of the invention to provide an NMR pulse sequence which is optimal for use in the borehole environment.

It is a further object of the invention to provide an NMR pulse sequence from which T1, T2, and amplitude may be measured in the borehole.

It is another object of the invention to provide an NMR pulse sequence which permits porosity, permeability, and other formation evaluations to be made in an advantageous manner.

In accord with the objects of the invention, an optimal method for determining T1, T2, and amplitude with a borehole tool comprises combining a modified fast inversion recovery pulse sequence with a series of at least ten CPMG pulses so as to obtain many measurements which are a function of T1, T2 and amplitude where variables including the number of CPMG echoes gathered, the wait times before starting the pulse sequence, the recovery times after the initial one hundred eighty degree pulses, and the number of recovery and waiting times utilized are optimized. T1, T2, and amplitude, and hence porosity, permeability, and other formation parameters are then found according to equations which relate the variables to the measurements obtained.

In particular, a borehole tool such as described in U.S. Ser. No. 07/368,916 is placed down a borehole traversing a formation, and a volume of the formation is subjected to a static magnetic field and to an oscillating magnetic field which is controlled according to a pulse sequence which permits simultaneous measurement of T1 and T2. The preferred pulse sequence is:

$$[W_i - 180\tau_i - 90 - (t_{cp} - 180 - t_{cp} - \text{echo})_j]_i \quad (3)$$

where $j = 1, 2, \ldots J$. where J is the number of echoes collected in the CPMG sequence and is typically on the order of one or two hundred, but always greater than ten; $i = 1, 2, \ldots I$, where I is the number of recovery times; $W_i$ are waiting times; $\tau_i$ are recovery times, and $t_{cp}$ is the Carr-Purcell spacing. Measurements of the signals induced in the formation as a result of the magnetic fields are made of each of a predetermined number of echoes. In the preferred embodiment, each echo measurement of the CPMG sequence is a measurement of the integrated amplitude of the echo, rather than a measurement of the greatest amplitude of the received echo. Determinations of T1, T2, and amplitude ($M_o$) are then made from the measurements. From one or more of the T1, T2, and amplitude determinations, formation parameters such as porosity and permeability may be derived according to equations known in the art.

In order to obtain the most accurate determinations of formation parameters in the least amount of time (as is required in the borehole setting), the various pulse sequence parameters, including the number of CPMG echoes measured, the wait times before starting the pulse sequence, the recovery times after the initial one hundred eighty degree pulses, and the number of wait and recovery times used are optimized. Optimization is possible if certain assumptions regarding the possible values of T1 are made. These assumptions may be made as a result of information gained from one or more initial measurements, or, where the general properties of the investigated object are known in advance (such as in the case with earth formations) the optimization can be made prior to obtaining the measurements.

Another preferred aspect of the invention is a change to the CPMG sequence utilized in measuring the echoes. Small baseline shifts in the measured signal can have serious effects on the accuracy of the measurement. In order to cancel any baseline shifts, the following CPMG sequence is utilized in successive repetitive experiments:

$$90(+x), [\text{tcp}, 180(y), \text{tcp}, \text{echo}]_j \quad (4a)$$

$$90(-x), [\text{tcp}, 180(y), \text{tcp}, \text{echo}]_j \quad (4b)$$

where x, y, and −x respectively represent zero, ninety, and one hundred eighty degree phase shifts with respect to a continuous wave Larmor frequency signal, and where the signal obtained from (4b) is subtracted from the signal obtained from (4a). If desired, third and fourth sequences $$90(+x) \quad (4c)$$

$$90(-x) \quad (4d)$$

may also be conducted in repetitive experiments (i.e. the recovery and wait times are the same), wherein signal 4c is subtracted from the difference of signals 4a and 4b, and signal 4d is added thereto.

Additional objects and advantages will become apparent to those skilled in the art upon reference to the detailed description taken in conjunction with the provided Figures.

BRIEF DESCRIPTION OF THE DRAWINGS

FIG. 4 is a flow chart in block diagram form of the preferred method inventions.

DETAILED DESCRIPTION OF THE PREFERRED EMBODIMENT

Figure 1:
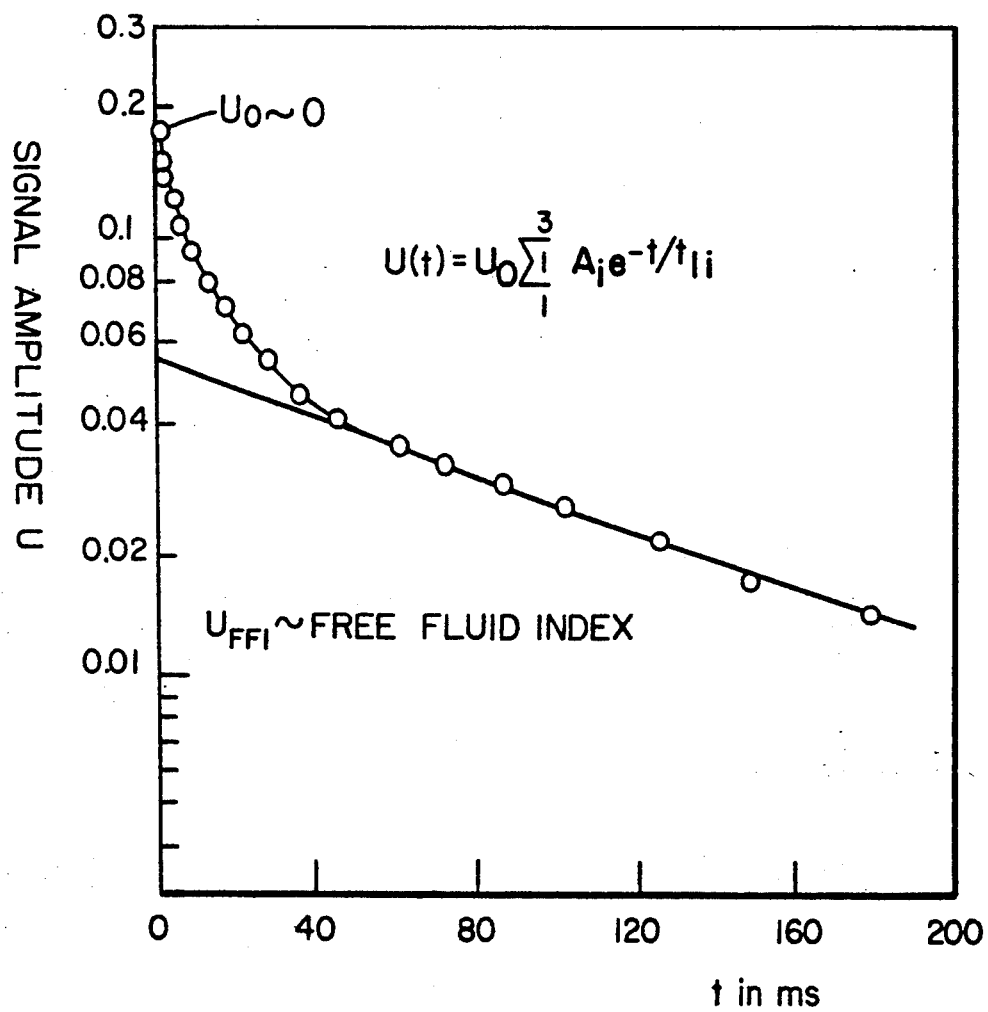
FIG. 1 is a prior art plot of an induced NMR signal detected from a formation having both free and bound fluids.
Figure 2:
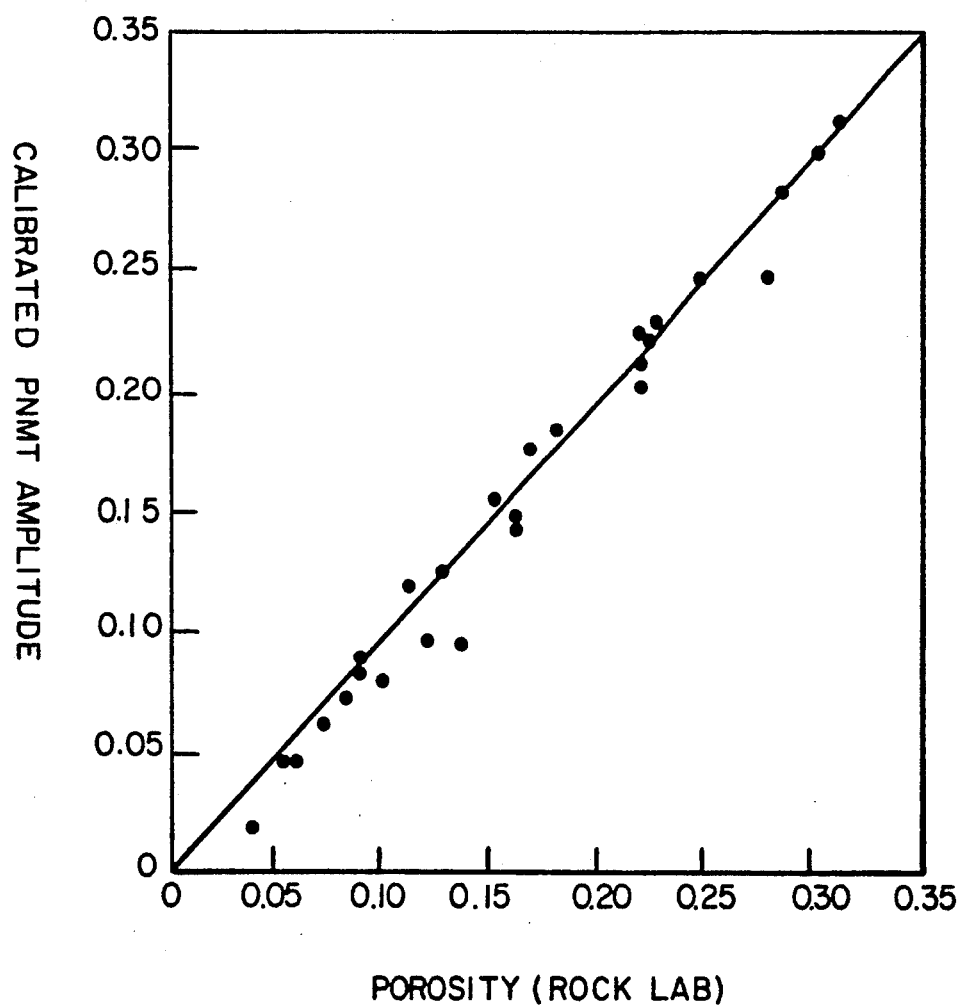
FIG. 2 is a plot showing the relationship of the amplitude of a detected signal of an NMR tool with the porosity of many different core samples.
Figure 3A:
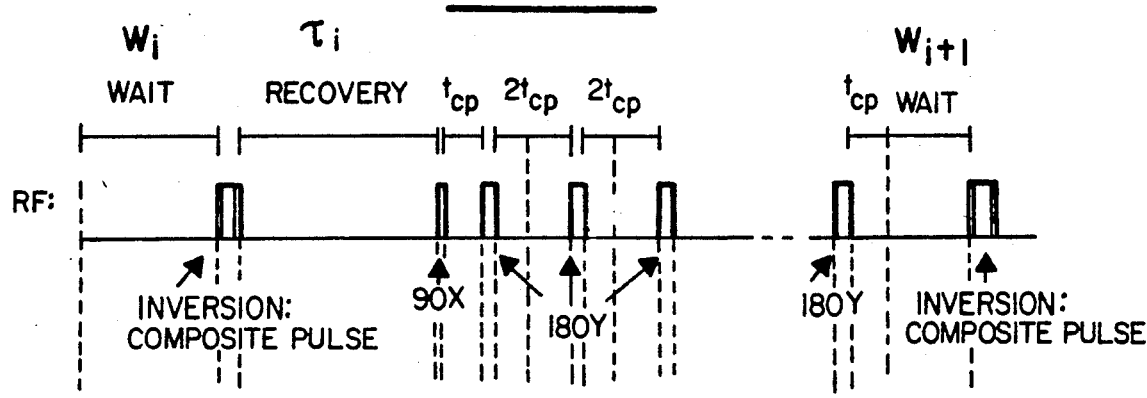
FIGS. 3a, 3b and 3c are graphs over time respectively of the pulse sequence of the invention, and the resulting longitudinal magnetization and measurable signal.
Figure 3B:
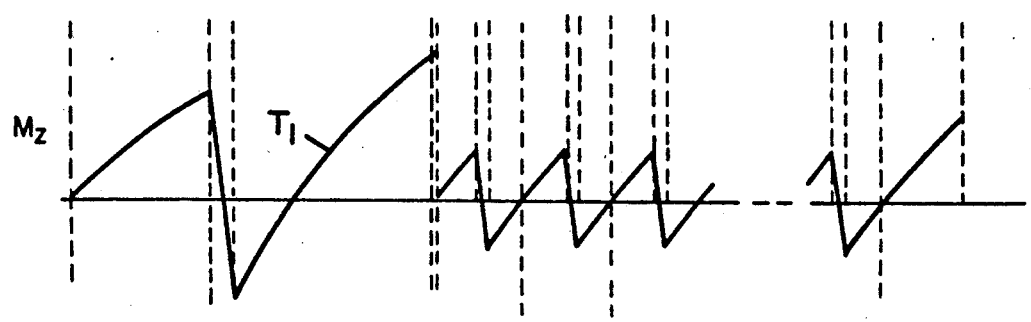
Figure 3C:
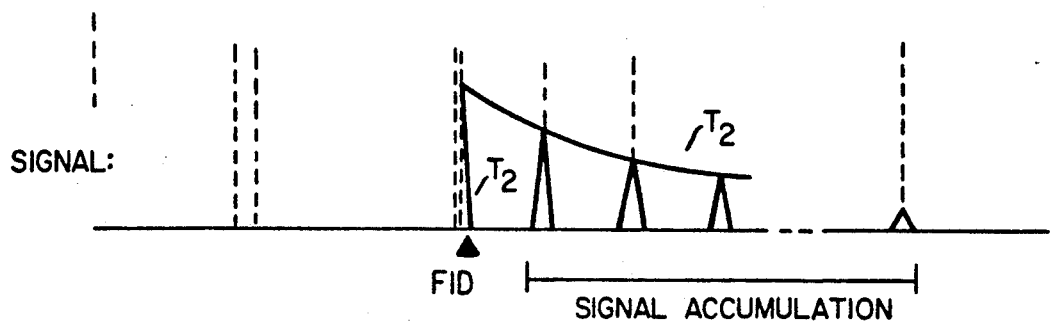

Turning to FIGS. 3a–3c, the preferred pulse sequence set forth by (3) above and conducted by the borehole tool of SN 07/368,916, is seen in graphics form. At the start of any (e.g. i'th) sequence after waiting for a waiting period $W_i$, the spin system is at zero transverse magnetization (as seen in FIG. 3c) and at a positive longitudinal magnetization which is less than the full equilibrium magnetization (as seen in FIG. 3b). When a pulse of one hundred eighty degrees is applied, the spins are inverted. However, no signal is observed during this time period, because the spins are along the static field and do not induce any signal in a measurement coil of the borehole tool. After the one hundred eighty degree pulse, and during the so-called recovery time $\tau_i$, the nuclear magnetization of the formation under investigation begins to relax towards the direction dictated by the static field. The rate at which a nuclear spin returns toward the static field is governed by the spin lattice relaxation time (T1) which is of great interest.

After pausing for the recovery time $\tau_i$, a ninety degree pulse is applied to the formation, causing the spins which have relaxed somewhat (according to the decay T1) to tip into the measurement plane where they generate a free induction decay (FID) signal in the measurement coil of the borehole tool. Because the deadtime of the borehole tool is on the order of fifty microseconds which is longer than the free induction decay time, the FID is not observed. However, by using the ninety degree pulse as the first pulse in a Carr-Purcell-Meiboom-Gill sequence, and as will be explained shortly, indications of T1 and T2 are obtained.

At a time $t_{cp}$ (Carr-Purcell time) after the ninety degree pulse, a one hundred eighty degree pulse is applied, and as seen in FIG. 3a, further one hundred and eighty degree pulses (known as refocussing pulses) are applied every $2t_{cp}$ in accord with the CPMC sequence. These one hundred eighty degree pulses generate measurable echoes at times $t_{cp}$ after each refocussing pulse. As indicated in FIG. 3c, the magnitude of the echoes decays over a period of time. The rate of decay is dictated by the spin-spin or T2 relaxation parameter. By applying many one hundred eighty degree pulses, numerous echo points are available for providing a decay curve indicative of T2. These numerous echoes permit a more accurate determination of the T1 relaxation parameter which is not obtainable otherwise.

The proposed preferred sequence has two main advantages over conventional (e.g. inversion recovery) methods of measuring T1. First, the proposed method does not depend on a measurement of a free induction decay which is lost in the instrumental deadtime of a borehole tool. Second the amplitude information needed for the T1 determination consists of a multiplicity of echoes following each wait—inversion recovery segment instead of one FID determination. Since the waiting and recovery times are very time consuming, it is clearly advantageous to collect as much amplitude information as possible on each wait—inversion recovery cycle.

Around the time that the observed echoes die away (e.g. after on the order of one hundred to one thousand echoes), such that continued CPMG tipping provides no additional information, and at a time which may be particularly specified by the maximization technique to be discussed below, the CPMG sequence is stopped. At this point in time, and as seen in FIGS. 3b and 3c, the net transverse and the longitudinal magnetizations are effectively zero. Thus, the ending point of a first cycle of the provided pulse sequence meets the starting requirement that the state of the spin system be known at the start of each cycle. In other words, the end of the CPMG sequence provides a good initial condition for the next measurement cycle which starts with another waiting period $W_{i+1}$, followed by a one hundred eighty degree pulse, followed by a recovery time $\tau_{i+1}$, followed by a ninety degree tipping pulse which starts the CPMG sequence. This measurement cycle is repeated a number of times, with various values of the recovery times $\tau_i$ and waiting times $W_i$. The preferred method of selection of the pulse parameters $W_i$, $\tau_i$, $t_{cp}$, and the number of echoes J in each CPMG sequence is described in detail below, as is the method for obtaining T1 and T2 from the data. The pulse sequence for purposes of brevity is referred to as the Fast Inversion Recovery/CPMG sequence, or FIR/CPMG, and is set forth in NMR notation in (3) above. Also, for purposes of definition, in the FIR/CPMG sequence of the invention, at least ten echoes, and typically on the order of hundreds of echoes are gathered during the CPMG part of the sequence.

In the preferred manner of collecting data, the echoes gathered during the CPMG part of the FIR/CPMG sequence are integrated individually or collectively by analog techniques, and the voltage of the integrator of the NMR borehole tool is read one or more times and stored. The integration of the echoes further accelerates signal accumulation as opposed to the usual technique of measuring the amplitude of each echo. To avoid accumulating pulse feedthrough and noise, the integrator is gated so that only the echoes themselves are integrated. For each borehole tool there is a spectrometer dependent optimal gating and an optimal value of $t_{cp}$ (which can be determined through straight-forward experimentation) that maximize the signal to noise ratio of the integral of the echoes. The performance of the optimal integrator is better than or equal to the performance of a one point amplitude measurement under all conditions. The quantitative advantage depends on the receiver deadtime, receiver bandwidth, and the spectrum of the nuclear signal. Preferably, the output of the integrator is read at multiple points during each CPMG sequence. If reduction of the data set is desired, the output of the integrator may be read only at the end of each CPMG sequence, in preparation for the next cycle of FIR/CPMG. However, in such a situation, the signal obtained from the formation should be analyzed as a single exponential signal.

The FIR/CPMG sequence has been found by the inventors to provide the most efficient manner of making T1 and T2 determinations, particularly in earth formations where the T2/T1 ratio is expected to be between 0.1 and 1. As a result, FIR/CPMG is the most advantageous sequence for use by a borehole tool. In fact, FIR/CPMG is more efficient than the FIR sequence presently being utilized in the material characterization arts by a factor of $T2/2t_{cp}$ which amounts to a factor of approximately two hundred for a typical logging tool in a typical earth formation. However, in order to recognize such a large increase in efficiency, the afore-described parameters of the FIR/CPMG sequence should be optimized to minimize the variance of the estimated parameters.

Measurements made by means of a borehole NMR measurement tool on simple samples such as water can be well described by the following equations:

$$y_{ij} = f_{ij} + n_{ij} \quad (5)$$

$$f_{ij} = M_o\{1 + (exp(-\tau_i/T1))(c - 1 - c(exp(-W_i/T1)))\}exp(-2t_{cp}j/T2) \quad (6)$$

$$x = (M_o, T1, T2) \quad (7)$$

$$z = (\tau_1, \ldots, \tau_J, W_1, \ldots, W_I, J, I) \quad (8)$$

$$T(z_I) = \sum_{i=1}^{I} (W_i + \tau_i + 2t_{cp}J) \quad (9)$$

where each y is the measured signal obtained during a CPMG echo, for J echoes and I recovery times, f is the deterministic part of y, n is the noise part of y, $M_o$ is the measured intensity of the spin echo when the transverse magnetization is as large as the equilibrium value of the longitudinal magnetization (i.e. $M_o$ is proportional to the equilibrium value of the longitudinal magnetization), c is an instrument constant, x is a vector of parameters which are unknown and which affect the measured signal y, z is the vector of known and deterministic parameters (e.g. the durations between pulses) that are controlled by the experimenter and are preferably chosen according to an optimization scheme described below, $T(z_I)$ is the minimum time required to acquire the data (measured signal y), and $W_i$, T1, T2, $t_{cp}$ and $\tau_i$ are as described with reference to (3) above. It should be appreciated that equation (5) derives from the fact that the signals measured are a function of both an induced signal and noise. Equation (6) is a simplified single exponential decay model which provides the relationship between the induced signal, the signal amplitude as it relates to the object under investigation, and the relaxation times of the object under investigation. Equation (6) therefore permits the parameters of interest, Mo, T1, and T2, to be estimated from the measured signals y via a nonlinear least square fit.

Because noise is part of the signal measurement as shown by (5) above, account must be taken thereof. Experiments indicate that the noise $n_{ij}$ is a Gaussian variable of zero mean, $$<n_{ij}> = 0 \quad (10)$$

and that the noise(s) associated with the recording of individual echoes are uncorrelated:

$$<n_{ij} n_{kl}> = \sigma^2 \sigma_{ik} \sigma_{jl} \quad (11)$$

where $\sigma_{ik}$ and $\sigma_{jl}$ are equal to one when indices are identical and equal to zero otherwise, and where $\sigma^2$ is the variance of the integral of a single spin echo $y_{ij}$.

Using equations (5)–(11), those skilled in the art will appreciate that determinations of $M_o$, T1 and T2 can be made via a non-linear least squares fit of obtained measurements, provided the instrument constant c is known. The instrument constant c is the cosine of the nutation angle produced by the rf pulses that are intended to tip the spins by one hundred eighty degrees. For a perfect instrument, the constant c is $-1$.

Once $M_o$, T1, and T2 are known, determinations of porosity, permeability, irreducible water saturation, etc. may be derived according to any of several known relationships as will be discussed hereinafter, provided the amplitude $M_o$ can be stated in calibrated porosity units. To provide a calibrated $M_o$, it should be recognized that the amplitude $M_o$ is proportional to the product of the total fluid filled porosity ($\phi$) and the density of hydrogen atoms ($n_H$) in the fluid relative to water according to the relationship $$M_o = a \phi n_H \quad (12)$$

where a is an instrument constant. To determine a and c, a measurement is performed on a water sample of known NMR parameters, and a and c are inverted from the data. The proportionality constant $a = M_o$ for water.

While equation (6) can be used in conjunction with a non-linear least square fit to provide a determination of $M_o$, T1, and T2 for a formation, it should be recognized that the NMR relaxation in rock samples is usually not a simple exponential. Rather, rock samples often contain pores of different sizes which provide different T1 relaxations. Information regarding distribution of pore sizes is important for a determination of formation parameters such as irreducible water saturation. To account for different pore sizes, equation (6) can be reformulated according to:

$$f_{ij} = \sum_{k=1}^{K} M_{ok}\{1 + e^{-\tau_i/T1k}(c - 1 - ce^{-W_i/T1k})\}e^{-2t_{cp}j/T2k} \quad (13)$$

where there are K groupings of pore sizes. In this K-exponential reformulation, there are 3K parameters (i.e. K values for $M_o$, T1, and T2), for which values must be determined. Using the borehole NMR instrument of copending U.S. Ser. No. 07/368,916, and a non-linear least square fit, it has been found that for a stationary tool, any number of values for $M_o$, T1, T2 can be determined given a large enough value for I, while for a typical moving tool, only two or possibly three values (i.e. K=2, 3) can be determined.

An alternate representation of equation (13) employs a continuous superposition of single exponentials in accord with a theory for inversion recovery presented by Kenyon, et al., *SPE Formation Evaluation*, Sept. 1988 (pp. 622-636), in which T1 is continuously distributed according to the density function:

$$P(\nu) = 0 \text{ if } \nu < 0, \text{ and } P(\nu) = exp[-(\nu/\nu_o)^{\alpha/(1-\alpha)}] \text{ if } \nu \geq 0 \quad (14)$$

where $P(\nu)\Delta\nu$ is proportional to the fraction of nuclear magnetization whose relaxation time is between $\nu$ and $\nu + \Delta\nu$, for an infinitesimal increment $\Delta\nu$. $\nu_o$ and $\alpha$ are parameters that control the shape of the distribution.

Under the assumption of (14), the inversion recovery measurement is described by a stretched-exponential formula:

$$f = M_o(1 - 2\exp[-(\tau/T1\alpha)^\alpha]) \quad (15)$$

Equation (15) corresponds to the case of the waiting times $W_i$ equalling infinity, and does not include CPMG sequences. Therefore, equation (15) is not directly applicable to the FIR/CPMG measurement. However, by fitting obtained rock data, the following preferred stretched-exponential representation for the FIR/CPMG measurement has been found :

$$f_{ij} = M_o\{\exp[-(2t_{cp}j/T2\alpha)^{\alpha 2}] + (c-1)\exp[-((\tau_i/T1\alpha) + (2t_{cp}j/T2\alpha))^{\alpha 1}] - c\exp[-(((\tau_i + W_i)/T1\alpha) + (2t_{cp}j/T2\alpha))^{\alpha 1}]\} \quad (16)$$

with equation (16), parameters $M_o$, $T1\alpha$, $T2\alpha$, $\alpha 1$, and $\alpha 2$, are determined via a non-linear least square fit of the data. Those skilled in the art will appreciate that equation (16) reduces to equation (6) when $\alpha 1 = \alpha 2 = 1$, and that for small $2t_{cp}j/T2\alpha$ and $c = -1$, equation (16) agrees with the stretch-exponential theory of inversion recovery set forth by equation (15). Moreover, for large $\tau_i/T1\alpha$, the last two terms of equation (16) are negligible, and the remaining first term describes a stretch-exponential spin-spin relaxation.

As aforementioned, in order for the FIR/CPMG sequence to be used to full advantage, the parameters $W_i$, $\tau_i$, I, and J are chosen according to an optimization scheme explained below. The optimization scheme has as its goal a choice of the parameters which will provide the most accurate determination of T1 and amplitude ($M_o$), and hence porosity, permeability, etc. in a given time. Such an optimization is particularly advantageous in the borehole environment as discussed in the Background section above.

Looking briefly at the basis of the optimization of the vector z parameters, if there are $T_o$ seconds allocated for a measurement, according to (9) above, $T_o/T(z_I)$ sets of data can be acquired to reduce the variance of observation. When $N = T_o/T(z_I)$ sets of FIR/CPMG data are collected, the vector of unknown parameters, x, is estimated by nonlinear least squares from the average of the data sets as $$\hat{x} = \underset{x}{\text{argmin}} \sum_{i=1}^{I} \sum_{j=1}^{J} \left( f_{ij}(x) - (1/N) \sum_{n=1}^{N} y_{ijn} \right)^2 \quad (17)$$

where $y_{ijn}$ denotes the i,jth echo in the nth data set, and argmin means "the argument that minimizes the following function." The inventors verified by experimentation that the variances of the estimated parameters are approximately equal to the Cramer-Rao lower bounds for the variances of the estimates, which are computed according to $$\text{Var}[\hat{x}_n] \simeq (T(z)/T_o)\text{CRLB}[\hat{x}_n], \quad (18a)$$
$$\text{CRLB}[\hat{x}_n] = \sigma^2(F^{-1})_{nn}, \quad (18b)$$

$$F_{pq} = \sum_{i=1}^{I} \sum_{j=1}^{J} \frac{\partial f_{ij}}{\partial x_p} \frac{\partial f_{ij}}{\partial x_q} \quad (18c)$$

where CRLB $[\hat{x}_n]$ denotes the Cramer-Rao lower bound for the variance of the estimate of $\hat{x}_n$ based on a single observation of the FIR/CPMG measurement. CRLB $[\hat{x}_n]$ is proportional to the nth diagonal entry of the inverse of the sensitivity matrix F, which is a square matrix and has as many columns and rows as the number of unknown variables. The derivatives in (18c) are obtained by differentiating $f_{ij}$ in either the single exponential model of relationship (6), the multi-exponential model of relationship (13), or the stretch exponential model set forth in (16) with respect to the unknown variables. The optimal sequence is specific to the relaxation model that is employed. The theory of Cramer-Rao lower bound is explained in "Detection, Estimation, and Modulation Theory" by H. L. Van Trees (Wiley, 1968), and in "Parameter Estimation" by H. W Sorenson (Marcel Dekker, 1980)

If $T(z_I)$ is increased in order to accommodate an increased number of CPMG sequences, while additional data are obtained on the one hand, fewer total cycles are accomplished resulting in decreased information on the other hand. It is desirable to optimize some combination of the variance (18a) of the estimates The preferred cost function for optimizing the vector z parameters is:

$$\text{COST} = (\text{Meas. time}) \times \left\{ \sum_{m=1}^{M} [c_0 \text{CRLB}(M_o)/a^2 + (c_1 \text{CRLB}(T1)/T1^2) + (c_2 \text{CRLB}(T2)/T2^2) \mid T1 = T1(m)]^n \right\}^{1/n} \quad (19)$$

where T1(1), T1(2), . . . , T1(M) are logarithmically spaced to cover the expected range of T1, and $c_0$, $c_1$, and $c_2$, are coefficients. In the preferred embodiment, $c_0$ is set equal to one, and $c_1$ and $c_2$ are set equal to 0.01. Weighting coefficients $c_1$ and $c_2$ are set one hundred times smaller than $c_0$ because ten percent accuracy is sufficient for the decay times, whereas porosity must be determined with an absolute accuracy of 0.01. Other values of $c_0$, $c_1$, and $c_2$ can be selected depending on the purpose of the measurement. For example, to measure porosity only, the weighting coefficients should be set to $c_0 = 1$, $c_1 = 0$, and $c_2 = 0$. The integer n is set equal to the value eight in the preferred embodiment. A large value of n is chosen to emphasize the largest error over the range of expected T1 values.

A computer program for conducting optimization of numerous variables which is useful in such circumstances may be obtained from IMSL, Inc. of Houston, Texas as the ZXMWD subroutine of a constraint optimization routine. The purpose of the routine is to minimize a cost function such as that of (19) above.

The time for an entire FIR-CPMG sequence (i.e. the Meas. time of equation (19)—also called $T(z_I)$ is dependent on the z vector parameters, including the number I and lengths $W_i$ of waiting periods, the lengths of recovery times $\tau_i$, and the number J of CPMG pulse echoes accumulated (the time factor relating to J equalling the number of echoes accumulated multiplied by $2t_{cp}$), and these parameters are varied by the computer program within reasonable limits set by the programmer (to limit computer processing time) so that optimal values for the z vector parameters can be determined. In particular, it should be noted that while "reasonable limits"

would suggest themselves to those skilled in the arts, it has been found by the inventors that for making optimal T1 and T2 measurements of the formation via use of a borehole tool, the number J of echoes accumulated should preferably be on the order of one hundred to one thousand and always more than ten (which essentially distinguishes the pulse sequence from similar sequences used in the medical arts), while the number of times I that the entire FIR-CPMG sequence is repeated is preferably on the order of three to six times, although limits might be set at one to sixty. The exact numbers of echoes and repeats, and the particular waiting and recovery times which should be associated with repeated measurements are obtained from the optimization conducted by the computer.

Those skilled in the art will appreciate that the particular optimization program or routine utilized is not critical for purposes of the invention. Neither is the exact cost function which preferably (for purposes of getting an optimal solution over the entire possible range of T1 in the borehole) utilizes an eighth root of an eighth power function. However, for the preferred aspect of optimizing the FIR-CPMG sequence, the basic concept of minimizing cost which is equal to the measurement time times a linear combination of the squares of the fractional uncertainty in estimating T1 and T2. The cost function is minimized by permitting the z vector variables which dictate the measurement time to vary. Also, while the optimization aspect of the preferred embodiment of the invention may be practiced by varying only certain of the z vector variables, preferably, all of the z vector variables are varied to determine the optimal values for each variable.

Baseline shifts can have a very serious effect on the accuracy of the measurement. Baseline shifts can arise from "phase glitches" and from inhomogeneities in the static and RF magnetic fields. They can also result from magnetoacoustic ringing effects. Electronic drifts that are not coherent with the pulses are another concern.

There are four contributions to the received voltage in the echo window. The first (S) is the signal from the resonated nuclear spins and is the desired signal for detection. The phase of S is determined by the phase of the initial ninety degree pulse in the CPMG sequence. The second contribution (R) is the result of any baseline effects generated by the one hundred eighty degree pulses which are not influenced by the phase of the ninety degree pulse. Phase glitch and field inhomogeneity effects, and magnetoacoustic ringing from the one hundred eighty degree pulses fall in this category. The third contribution (r) is produced by the ninety degree pulse and is phase coherent with it. Magnetoacoustic ringing from the ninety degree pulse falls into this class. The last contribution is an electronic baseline (B), which may vary slowly as a function of time, and whose phase does not depend on the phases of the various pulses. The phase coherence characteristics of the undesired contributions make it possible to electronically cancel them according to the following cycle which is preferably used in repeated experiments in the FIR/CPMG sequence:

$$90(+x) - [t_{cp} - 180(y) - t_{cp} - echo]_j \quad S + R + r + B \quad (20)$$

$$90(-x) - [t_{cp} - 180(y) - t_{cp} - echo]_j \quad -S + R - r + B \quad (21)$$

$$90(+x) \quad r + B \quad (22)$$

-continued $$90(-x) \quad -r + B \quad (23)$$

where x, y, and −x represent respectively zero, ninety, and one hundred eighty degree phase shifts with respect to a continuous Larmor frequency signal. Subtracting the results of the second set of experiments from the first set provides a signal of $2S+2r$. Subtracting the fourth set of experiments from the third set provides a signal of $2r$. Subtracting the $2r$ from the $2S+2r$ (i.e. combining the experiments by adding the first and fourth, and subtracting therefrom the second and the third) provides the desired signal free from baseline shifts. It should be appreciated that if the effect of ringing after the ninety degree pulse is negligible, the third and fourth sets of the sequence are not needed. The two sequence cycle ((20) and (21)) is adequate to eliminate baseline and one hundred eighty degree ringing problems, and the inclusion of sets the third and fourth set merely eliminates the initial transient, which has usually decayed before echo integration.

Turning to FIGS. 4 and 5a–5c, a flow chart of the practice of the preferred embodiment of the invention, and results obtained in a laboratory test are provided. Prior to the disclosed in Ser. No. 06/901,084 was calibrated at 110 by performing an FIR/CPMG measurement on a NiCl doped water sample to determine the tool constants a and c. The tool constants were determined to be $a=7.58$ and $c=-0.59$. At 120, an optimization program was run in accord with (18) and (19) to produce two pulse sequences: one for low range T1 values; and one for the high range T1 values, although only the high range T1 values are treated hereafter. The reason for breaking up the T1 range into two sections is that the error performance of each pulse sequence in its respective range is superior to that of a pulse sequence that covers the entire range of T1 values. The pulse sequence to be utilized was obtained by optimizing the performance of the pulse sequence for the following set of stretched-exponential relaxation parameters porosity $=14$PU, $t_{cp}=200$ microseconds, $\alpha1=0.622$, $\alpha2=0.535$, $T1\alpha/T2\alpha=1.8$, and $T1(m)=0.0316, 0.0500, 0.0792, 0.1256, 0.1991, 0.3155, 0.5000$ seconds. The resulting sequence had the following parameters: $I=5$, $J=794$, $W_1=0.490$, $W_2=0.000$, $W_3=0.000$, $W_4=0.000$, $W_5=1.048$, $\tau_1=0.024$, $\tau_2=0.242$, $\tau_3=0.243$, $\tau_4=0.243$, and $\tau_5=0.036$. The total FIR/CPMG with phase alternation sequence measurement time equals 7.829 seconds.

Figure 5A:
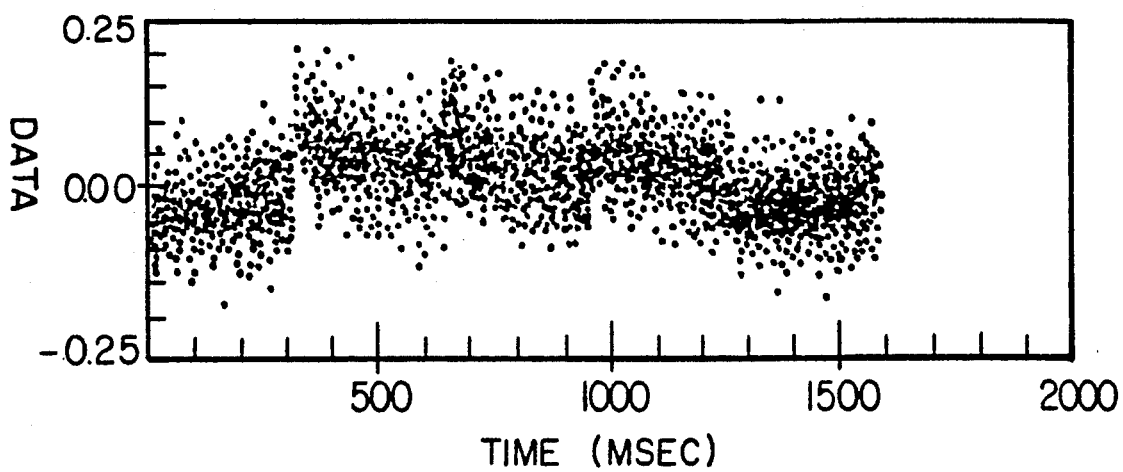
FIGS. 5a, 5b and 5c are respectively the echo measurements of a FIR/CPMG sequence, five curves which were fitted to the measurements of FIG. 5a, and the differences between the points represented in FIGS. 5a and 5b.
Figure 5B:
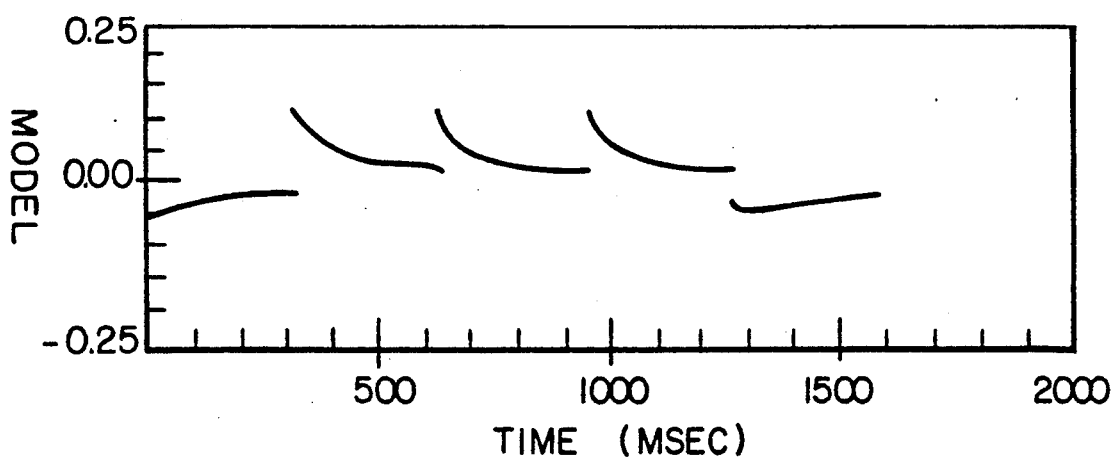
Figure 5C:
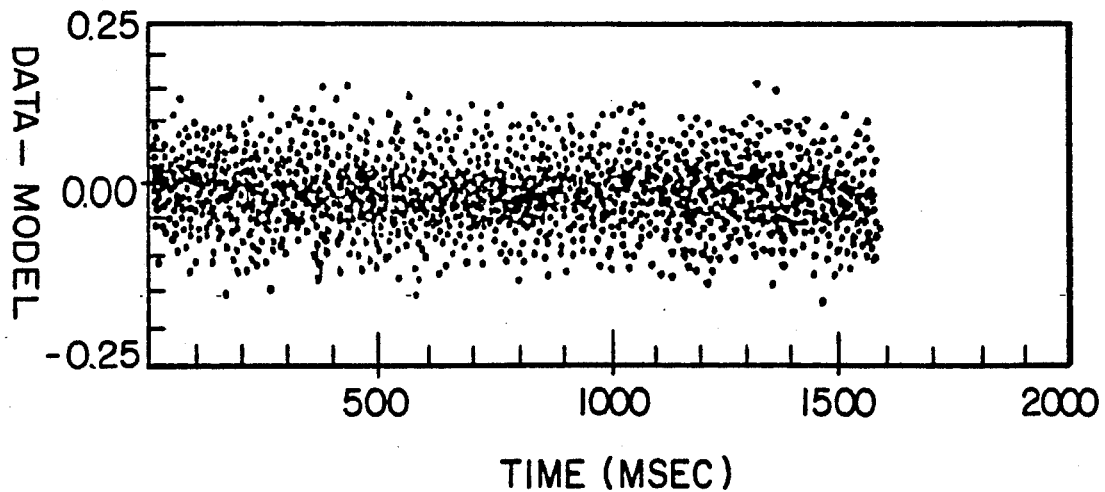

At 130, the parameters of the long T1 sequence were entered into the measurement apparatus, and at 140, a water saturated sandstone sample was placed in the sensitive region of the apparatus. The FIR/CPMG pulse sequence with phase alternation (see (20)–(21) above) was conducted by the apparatus and the spin echoes were recorded at 150. The sequence was repeated twice and the two data sets were averaged. The resulting data points are shown in FIG. 5a. Two sets of data were collected in 15.66 seconds, during which a tool logging at nine hundred feet per hour would have moved forty-seven inches (1.19 meters). According to one preferred method of the invention, the parameters $M_o$, $T1\alpha$, and $T2\alpha$ of the stretched exponential model were estimated from the average of the two data sets using nonlinear least square minimization at step 160b, assuming that $\alpha1=0.62$, $\alpha2=0.54$, and $c=-0.59$. The nonlinear least square minimization of step 160b provided the curves of FIG. 5b, with FIG. 5c (which has points scattered about zero) showing the difference between the average of the measured values of FIG. 5a and the curves of FIG. 5b.

In order to assess the effects of random error (noise), the process of conducting two FIR/CPMG sequences with phase alternation, and estimating porosity, T1α, and T2α, was repeated eighty times at steps 150 and 160b. Porosity was then determined at 170b according to the equation $$\phi = M_o/a \quad (24)$$

where $\phi$ is the porosity in porosity units, $M_o$ is the determined signal amplitude at step 160b, and a is the previously discussed tool constant.

In accord with the provided pulse sequence and equations (16), (17), and (24), the sample mean and variation of the estimated porosity, T1α, and T2α, were found at 170b to be:

|     | ACTUAL | MEAN OF EST. | STANDARD DEV. | CRAMER-RAO L.B. |
| --- | --- | --- | --- | --- |
| $\phi$ | 0.189 | 0.189 | 0.006 | 0.007 |
| T1α | 0.192 | 0.192 | 0.011 | 0.012 |
| T2α | 0.157 | 0.157 | 0.010 | 0.012 | where $\phi$ is in porosity units, and T1α and T2α are in seconds. The parameters in the first column are estimated from the average of all one hundred sixty measurements and therefore contain negligible statistical error. The second and third columns indicate the mean and standard deviation therefrom of the eighty determinations of $M_o$, T1α, and T2α. The last column is the Cramer-Rao lower bound of the estimated parameters computed as previously explained. As seen from the above table, there is negligible statistical bias in the estimates, and the error performance of the estimation is close to its theoretical limit.

Using the porosity and T1 determinations in accord with the above table, a permeability determination for the rock sample was made at 170b in accordance with Kenyon et al.'s formula (SPE 15643, 1986):

$$\text{permeability} = 5{,}060{,}000 \times (T1\alpha)^{2.3} \times \phi^{4.3} \quad (25)$$

where T1α is in seconds, and porosity is dimensionless and between zero and one. According to equation (25), the permeability of the sample was eighty-eight millidarcies with an uncertainty factor of 2.65. Thus, the determined permeability is estimated as between thirty-three and two hundred thirty-three millidarcies.

As indicated at steps 160a, 170a, and 160c and 170c, other methods of determining porosity and permeability are also available. In particular, where a multiple exponential model is utilized, the porosity is found as a sum:

$$\phi = \sum_{k=m}^{n} M_{ok}/a \quad (26)$$

while permeability is preferably found in accord with Kenyon et al. [SPE 15643, 1986] as:

$$k(\text{in } mD) = K(1000 T1>)^{s1}(100 M_o>/a)^{s2} \quad (27)$$

For a two-exponential fit, $T1>$ is the longer of the two spin-lattice relaxation times, $M_{o>}$ is the amplitude of the component with the longest relaxation time, and K, s1 and s2 are preferably set as $K = 3.6 \times 10^{-9}$, $s1 = 2.09$, and $s2 = 4.61$. For the three exponential fit, $T1>$ is the longest of the three spin-lattice relaxation times, $M_{o>}$ is the amplitude of the component with the longest relaxation time, and K, s1 and s2 are preferably set as $K = 2.8 \times 10^{-7}$, $s1 = 1.77$ and $s2 = 4.03$. It will be appreciated that equation (27) reduces to equation (25) for the stretched exponential case and the determined values where $T1> = T1\alpha$, $M_{o>} = M_o$, $K = 1.9 \times 10^{-9}$, $s1 = 2.31$, and $s2 = 4.30$.

Other techniques for determining permeability from T1 and $M_o$ determinations are set forth in Seevers, *SPWLA Transactions*, 1966, No. 6, Section L, and Timur, *Journal of Petroleum Technology*, 1969 (pp 775–786) which are referenced in the Background section herein. In fact, according to Timur, permeability relates to the porosity and irreducible water saturation which can be determined as:

$$S_{wirr} = 1 - FFI \quad (28a)$$

$$FFI = M> /(M_{oa} + M_{ob} + M_{oc}) \quad (28b)$$

where FFI is the free fluid index, and where $M>$ is obtained by summing the amplitudes $M_{ok}$ of the exponential components whose T1k exceed a threshold value $T_{crit}$ which Timur chose as twelve milliseconds.

To determine the effectiveness of the method invention, the porosity, T1, and permeability determinations of the method invention were compared to corresponding measurements made on the sample rock in different manners. Thus, a porosity measurement of the rock was made according to the buoyancy method; a permeability measurement was made by flowing water through the sample rock; and a T1 measurement was made using a commercially available NMR apparatus and the standard inversion recovery pulse sequence. Comparisons between the determinations of the method invention and the measurements using other techniques shows relatively close agreement which confirms the usefulness of the method invention. A comparison of the porosity determination of the method invention of $18.9 \pm 0.7$ PU to the $18.5 \pm 1.5$ PU measurement of the buoyancy method shows the method invention determination to fall within the buoyancy method bounds. Similarly, the T1 determination of 0.189 was within seven percent of the inversion recovery measurement. The permeability estimate of 88 millidarcies is within a factor of 3.5 of the $308 \pm 25$ mD laboratory measured result. This is considered accurate for borehole logging techniques.

Because the rock sample was investigated out of the borehole, a determination of residual oil saturation was not made. However, in the borehole, residual oil saturation can be determined by running the NMR tool a first time to determine porosity according to relationship (24), saturating the formation water with manganese ions by circulating solubilized manganese ions in the drilling mud while swabbing or reaming, and then running the NMR tool a second time to again determine porosity. The residual oil saturation is then found as the difference in the porosity determinations ($\Delta\phi$).

It will be appreciated that in the borehole, continuous logs of porosity, permeability, irreducible water saturation, etc. can be derived from the NMR tool measurements by first determining the tool constants and optimal parameters prior to logging, and then repeating steps 140-170 which respectively utilize the FIR/CPMG sequence, measure the results, conduct a least squares fit of measured data, and transform the results into appropriate logs over a length of a borehole.

There have been disclosed and illustrated herein NMR pulse sequences which have advantageous use in conjunction with borehole tools. While particular embodiments have been presented, it is not intended that the invention be limited thereto, as it is intended that the invention be broad in scope and that the specification be read likewise. In particular, while certain equations have been set forth to describe the physics of NMR in the borehole, and the signal received by a borehole tool, those skilled in the art will recognize that different equations could be used as a model. Thus, the use of the particular equations set forth is intended to be illustrative rather than limiting. Similarly, while the borehole tool of choice for conducting the pulse sequence and measurements described is that of copending Ser. No. 07/368,916, other tools could suffice. Further, while particular relationships between the relaxation time T1, and the signal amplitude $M_o$ (and the stretch exponential parameters) with porosity, permeability, and other formation characteristics were set forth, it is not intended that the invention be limited thereto. Rather, the invention is intended to encompass determination of any formation characteristics where the characteristics can be related to the NMR determinations.

It should also be appreciated by those skilled in the arts that advantageous results can be obtained where the waiting times of the FIR/CPMG sequence are reduced to the zero limit. In such circumstances there is no need for the inverting one hundred eighty degree pulse prior to the CPMG sequence. The resulting pulse sequence may then be described as saturation recovery/CPMG which is defined according to $$[\tau_i - 90 - (t_{cp} - 180 - t_{cp} - \text{echo})j]_i \quad (29)$$

and with echo amplitudes $$f_{ij} = M_o(1 - e^{-\tau_i/T1})e^{-2t_{cp}j/t2} \quad (30)$$

for the single exponential model. Analogous expressions for the stretch exponential and multi-exponential models will be apparent to those skilled in the art. With saturation recovery/CPMG, the recovery times, as well as the number of experiments (i.e. number of recovery times) and number of echoes in the CPMG sequence are preferably optimized according to the optimization technique set forth above.

In light of the above, it will be apparent to those skilled in the art that other changes and modifications may be made to the invention as described in the specification without departing from the spirit and scope of the invention as so claimed.

We claim:

1. A method for measuring an indication of an attribute of a volume of earth formation with a borehole tool having means for producing static magnetic fields in a volume of a formation, means for producing oscillating magnetic fields in a volume of a formation, and means for measuring an induced magnetic signal, said method comprising:

a) producing a static magnetic field in said volume of formation;

b) producing oscillating magnetic fields according to a pulse sequence $$[W_i - 180 - \tau_i - 90 - (t_{cp} - 180 - t_{cp} - \text{echo})j]_i$$

where $j = 1, 2, \ldots J$, and J is the number of echoes collected in a single Carr-Purcell-Meiboom-Gill (CPMG) sequence, where $i = 1, \ldots I$, and I is the number of waiting times used in the pulse sequence, where $W_i$ are recovery times before a CPMG sequence, and where $\tau_i$ are recovery times before a CPMG sequence, and where $t_{cp}$ is the Carr-Purcell spacing, in order to induce signals in said volume which are measurable by said tool in said borehole; and c) measuring with said tool said induced signals.

2. A method according to claim 1, further comprising:

d) determining from said measured signals an indication of said attribute of said volume of earth formation.

3. A method according to claim 2, wherein:
J is greater than or equal to ten.

4. A method according to claim 3, wherein:
J is greater than or equal to one hundred.

5. A method according to claim 4, wherein:
I is greater than or equal to two and less than or equal to sixty.

6. A method according to claim 3, wherein:
said induced signals comprise at least CPMG echoes, and said step of measuring said induced signals comprises integrating at least portions of said CPMG echoes.

7. A method according to claim 6, wherein:
said step of measuring said induced signals comprises gating the measurements measured by said tool, and integrating only desired of said portions of said CPMG echoes.

8. A method according to claim 1, further comprising:
repeating steps b and c for said volume of said formation, wherein in a first said pulse sequence, said 90 degree pulse is a 90(+x) pulse, and in a pulse sequence during said repeated step b, said 90 degree pulse is a 90(−x) pulse, where +x and −x denote the phase of the Larmor frequency of the carrier of the pulse with respect to a continuous wave Larmor frequency signal, and wherein results measured in step c and repeated step c are subtracted from each other to provide a corrected measurement.

9. A method according to claim 8, further comprising:
producing oscillating magnetic fields according to a pulse sequence $W_i - 180 - \tau_i - 90(+x)$ and measuring with said tool signals induced thereby, and producing oscillating magnetic fields according to a pulse sequence $W_i - 180 - \tau_i - 90(-x)$ and measuring with said tool signals induced thereby, wherein the measurements from said $W_i - 180 - \tau_i - 90(-x)$ are subtracted from said $W_i - 180 - \tau_i - 90(+x)$ measurement to provide a first difference, and said first difference is subtracted from said corrected measurement to provide a further corrected measurement.

10. A method according to claim 2, wherein:
said step of determining an indication of an attribute of said formation comprises determining at least a value for a spin-lattice relaxation time (T1) of said formation from said measured induced signals according to a relationship which relates at least T1 to the magnitude of said induced signals.

11. A method according to claim 10, further comprising:
before producing magnetic fields in said formation, choosing values for at least two of a group of variables consisting of I, J, $W_i$, and $\tau_i$, wherein said relationship which relates at least said spin-lattice relaxation time to the magnitude of said induced signals includes at least said two of a group of variables therein, and wherein the values of said at least two of a group of variables are chosen by optimizing said at least two of a group of variables in said relationship to reduce the variance of an estimate of T1 to a minimum.

12. A method according to claim 11, wherein:
said at least two of a group of variables are optimized by minimizing a cost function which includes a measurement time multiplied by a function of the uncertainty in estimates of at least T1, wherein the measurement time is a function of the variables of optimization.

13. A method according to claim 12, wherein:
said cost function ,is $$COST = (Meas.\ time) \times \left( \sum_{m=1}^{M} [c_0 CRLB(M_o)/a^2 + (c_1 CRLB(T1)/T1^2) + (c_2 CRLB(T2)/T2^2) \mid T1 = T1(m)]^n \right)^{1/n}$$

where $M_o$ is proportional to the equilibrium value of the longitudinal magnetization, CRLB denotes the Cramer-Rao lower bound for the variances of the estimates based on said measurements resulting from said pulse sequence, (Meas.time) is the time it takes to complete one pulse sequence, T1(1), T1(2), ..., T1(M) are logarithmically spaced time covering the expected range of T1, and $c_0$, $c_1$, and $c_2$ are predetermined coefficients.

14. A method according to claim 13 wherein:
n equals 8, $c_0 = 1$, and $c_1$ and $c_2 = 0.01$.

15. A method according to claim 13, wherein:
said at least two of a group of variables are $W_i$ and $\tau_i$.

16. A method according to claim 13, wherein:
said at least two of a group of variables are all of $W_i$, $\tau_i$, I and J.

17. A method according to claim 2, wherein:
said step of determining an indication of an attribute of said formation comprises determining at least a value for an amplitude parameter $M_o$ of said formation from said measured induced signals according to a relationship which relates at least $M_o$ to the magnitude of said induced signals, where $M_o$ is proportional to the equilibrium value of the longitudinal magnetization.

18. A method according to claim 10, wherein:
said relationship relates T1, T2, and $M_o$, to said induced signal, wherein T2 is the spin-spin relaxation time, and $M_o$ is proportional to the equilibrium value of the longitudinal magnetization.

19. A method according to claim 17, wherein:
said relationship relates T1, T2 and $M_o$ to said induced signal, wherein T2 is the spin-spin relaxation time, and T1 is the spin-lattice relaxation time.

20. A method according to claim 19, wherein:
said relationship which relates T1, T2, and $M_o$ to said induced signal is $$f_{ij} = Mo\{1 + (exp(-\tau_i T1))(c - 1 - c(exp(-W_i/T1)))\}exp(-2t_{cpj}/T2)$$

where $f_{ij}$ is said induced signal at the j'th echo after the i'th recovery time, and c is a constant relating to said borehole tool.

21. A method according to claim 20, wherein:
said step of determining a value for at least T1 comprises conducting a non-linear least squares fit to find values for T1, T2, and $M_o$ which fit said induced signal measurements to said relationship.

22. A method according to claim 19, further comprising:
e) from said determination of $M_o$ determining the porosity of said formation according to a second relationship which relates $M_o$ to porosity.

23. A method according to claim 2, wherein:
said step of determining an indication of an attribute of said formation comprises determining a spin-lattice relaxation time (T1k) of at least one component of said formation from said measured induced signals according to a relationship which relates T1k's to the magnitude of said induced signals.

24. A method according to claim 23, wherein:
said relationship relates T1k, T2k and $M_{ok}$ to said induced signal, according to $$f_{ij} = \sum_{k=1}^{n} M_{ok}\{1 + e^{-\tau_i/T1k}(c - 1 - ce^{-W_i/T1k})\}e^{-2tcpj/T2k}$$

wherein k varies from one to at least two, T2k are the spin-spin relaxation times associated with the respective components of said formation, the sum of $M_{ok}$ is proportional to the equilibrium value of the longitudinal magnetization, $f_{ij}$ is said induced signal at the j'th echo after the i'th recovery time, and c is a constant relating to said borehole tool 25. A method according to claim 24, wherein:
said step of determining a value for at least T1k comprises conducting a non-linear least squares fit to find values for T1k, T2k, and $M_{ok}$ which fit said induced signal measurements to said relationship.

26. A method according to claim 25, further comprising:
e) from said determinations of $M_{ok}$, determining the porosity of said formation according to a second relationship which relates $M_{ok}$'s to porosity.

27. A method according to claim 25, further comprising:
e) from said determinations of T1k, determining the permeability of said formation according to a second relationship which relates T1k to permeability.

28. A method according to claim 25, further comprising:
e) from said determinations of $M_{ok}$, determining the irreducible water saturation of said formation according to a second relationship which relates Mok's to irreducible water saturation.

29. A method according to claim 2, wherein:

said step of determining an indication of an attribute of said formation comprises determining at least a value for one of the stretch exponential spin-lattice relaxation time (T1α) of said formation and an amplitude $M_o$ parameter of said formation from said measured induced signals according to a relationship which relates said T1α and $M_o$ to the magnitude of said induced signals.

30. A method according to claim 29, wherein:
said relationship relates T1α, T2α, α1, α2, and $M_o$, to said induced signal, according to $$f_{ij} = M_o\{exp[-(2t_{cpj}/T2\alpha)^{\alpha 2}] + (c-1)exp[-((\tau_i/T1\alpha) + (2t_{cpj}/T2\alpha))^{\alpha 1}] - c\, exp[-(((\tau_i W_i)/T1\alpha) + (2t_{cpj}/T2\alpha))^{\alpha 1}]\}$$

wherein T2α is the stretched exponential spin-spin relaxation times associated with said formation, α1 and α2 are the stretch exponents, $M_o$ is proportional to the equilibrium value of the longitudinal magnetization, $f_{ij}$ is said induced signal at the j'th echo after the i'th recovery time, and c is a constant relating to said borehole tool.

31. A method according to claim 30, wherein:
said step of determining a value for at least T1α comprises conducting a non-linear least squares fit to find values for T1α, T2α, α1, α2, and $M_o$ which fit said induced signal measurements to said relationship.

32. A method according to claim 29, wherein said step of determining a value comprises determining at least $M_o$, said method further comprising:
e) from said determination of $M_o$, determining the porosity of said formation according to a second relationship which relates $M_o$ to porosity.

33. A method according to claim 29, wherein said step of determining a value comprises determining at least T1α, said method further comprising:
e) from said determination of T1α, determining the permeability of said formation according to a second relationship which relates T1α to permeability.

34. A method according to claim 20, further comprising:
before producing magnetic fields in said formation, choosing values for variables I, J, $W_i$, and $\tau_i$, wherein said relationship which relates at least said spin-lattice relaxation time to the magnitude of said induced signals includes said variables therein, and wherein said variables are chosen by optimizing the values of said variables in said relationship to reduce the variance of at least an estimate of T1 to a minimum.

35. A method according to claim 34, wherein:
values for said variables are optimized by minimizing a cost function $$COST = (Meas.\ time) \times \left\{ \sum_{m=1}^{M} [c_0 CRLB(M_o)/a^2 + (c_1 CRLB(T1)/T1^2) + (c_2 CRLB(T2)/T2^2) \mid T1 = T1(m)]^n \right\}^{1/n}$$

where $M_o$ is proportional to the equilibrium value of the longitudinal magnetization, CRLE denotes the Cramer-Rao lower bound for the variances of the estimates based on said measurements resulting from said pulse sequence, (Meas.time) is the time it takes to complete one pulse sequence, T1(1), T1(2), ..., T1(M) are logarithmically spaced time covering the expected range of T1, and $c_0$, $c_1$, and $c_2$ are predetermined coefficients.

36. A method according to claim 24, wherein:
before producing magnetic fields in said formation, choosing values for variables I, J, $W_i$, and $\tau_i$, wherein said relationship which relates at least said spin-lattice relaxation times to the magnitude of said induced signals includes said variables therein, and wherein said variables are chosen by optimizing the values of said variables in said relationship to reduce the variances of at least one of the T1k's to a minimum.

37. A method according to claim 32, wherein:
before producing magnetic fields in said formation, choosing values for variables I, J, $W_i$, and $\tau_i$, wherein said relationship which relates at least said stretched spin-lattice relaxation time to the magnitude of said induced signals includes said variables therein, and wherein said variables are chosen by optimizing the values of said variables in said relationship to reduce the variance of at least an estimate of T1α to a minimum.

38. A method according to claim 37, wherein:
values for said variables are optimized by minimizing a cost function $$COST = (Meas.\ time) \times \left\{ \sum_{m=1}^{M} [c_0 CRLB(M_o)/a^2 + (c_1 CRLB(T1\alpha)/T1\alpha^2) + (c_2 CRLB(T2\alpha)/T2\alpha^2) \mid T1\alpha = T1(m)]^n \right\}^{1/n}$$

where $M_o$ is proportional to the equilibrium value of the longitudinal magnetization, CRLB denotes the Cramer-Rao lower bound for the variances of the estimates based on said measurements resulting from said pulse sequence, (Meas.time) is the time it takes to complete one pulse sequence, T1(1), T1(2), ...,T1(M) are logarithmically spaced time covering the expected range of T1α, and $c_0$, $c_1$, and $c_2$ are predetermined coefficients.

39. A method according to claim 34, wherein:
J is greater than or equal to ten;
I is greater than or equal to two and less than or equal to sixty; and
said induced signals comprise at least CPMG echoes, and said step of measuring said induced signals comprises integrating at least portions of said CPMG echoes.

40. A method according to claim 36
J is greater than or equal to ten;
I is greater than or equal to two and less than or equal to sixty; and
said induced signals comprise at least CPMG echoes, and said step of measuring said induced signals comprises integrating at least portions of said CPMG echoes.

41. A method according to claim 38, wherein:
J is greater than or equal to ten;

I is greater than or equal to two and less than or equal to sixty; and said induced signals comprise at least CPMG echoes, and said step of measuring said induced signals comprises integrating at least portions of said CPMG echoes.

42. A method for measuring an indication of an attribute of a volume of earth formation with a borehole tool having means for producing static magnetic fields in a volume of a formation, means for producing oscillating magnetic fields in a volume of a formation, and means for measuring an induced magnetic signal, said method comprising:

a) producing a static magnetic field in said volume of formation;

b) producing oscillating magnetic fields according to a pulse sequence $$[\tau_i - 90 - (t_{cp} - 180 - t_{cp} - \text{echo})_j]_i$$

where $j = 1, 2, \ldots, J$, and J is the number of echoes collected in a single Carr-Purcell-Meiboom-Gill (CPMG) sequence, J being greater than or equal to ten, where $i = 1, \ldots I$, and I is the number of recovery times in the pulse sequence, where $\tau_i$ are recovery times, and where $t_{cp}$ is the Carr-Purcell spacing, in order to induce signals in said volume which are measurable by said tool in said borehole; and c) measuring with said tool said induced signals.

43. A method according to claim 42, further comprising:

d) determining from said measured signals an indication of said attribute of said volume of earth formation.

44. A method according to claim 43, wherein:

said induced signals comprise at least CPMG echoes, and said step of measuring said induced signals comprises integrating desired portions of said CPMG echoes.

45. A method according to claim 42, further comprising:

repeating steps b and c for said volume of said formation, wherein in a first said pulse sequence, said 90 degree pulse is a 90(+x) pulse, and in a pulse sequence during said repeated step b, said 90 degree pulse is a 90(−x) pulse, where +x and −x denote the phase of the Larmor frequency of the carrier of the pulse with respect to a continuous wave Larmor frequency signal, and wherein results measured in step c and repeated step c are subtracted from each other to provide a corrected measurement.

46. A method according to claim 43, wherein:

said step of determining an indication of an attribute of said formation comprises determining at least a value for at least one of a spin-lattice relaxation time (T1) of said formation and an amplitude $M_o$ of said formation from said measured induced signals according to a relationship which relates at least T1 and $M_o$ to the magnitude of said induced signals, wherein $M_o$ is proportional to the equilibrium value of the longitudinal magnetization.

47. A method according to claim 46, further comprising:

before producing magnetic fields in said formation, choosing values for at least two of a group of variables consisting of I, J, and $\tau_i$, wherein said relationship which relates at least said spin-lattice relaxation time to the magnitude of said induced signals includes at least said two of a group of variables therein, and wherein the values of said at least two of a group of variables are chosen by optimizing said at least two of a group of variables in said relationship to reduce the variance of an estimate of T1 to a minimum.

48. A method according to claim 47, wherein:

said at least two of a group of variables are optimized by minimizing a cost function which includes the product of a measurement time multiplied by a function of the uncertainty in estimates of at least T1, wherein the measurement time is a function of the variables of optimization.

49. A method according to claim 48, wherein:

said cost function is $$\text{COST} = (\text{Meas. time}) \times \left( \sum_{m=1}^{M} [c_0 CRLB(M_o)/a^2 + (c_1 CRLB(T1)/T1^2) + (c_2 CRLB(T2)/T2^2) \mid T1 = T1(m)]^n \right)^{1/n}$$

where $M_o$ is proportional to the equilibrium value of the longitudinal magnetization, CRLB denotes the Cramer-Rao lower bound for the variances of the estimates based on said measurements resulting from said pulse sequence, (Meas.time) is the time it takes to complete one pulse sequence, T1(1), T1(2), ..., T1(M) are logarithmically spaced time covering the expected range of T1, and $c_0$, $c_1$, and $c_2$ are predetermined coefficients.

50. A method according to claim 48, wherein:

said at least two of a group of variables are all of $\tau_i$, I and J.

51. A method according to claim 46, wherein:

said relationship relates T1, T2, and $M_o$ to said induced signal, wherein T2 is the spin-spin relaxation time, and T1 is the spin-lattice relaxation time.

52. A method according to claim 51, wherein said relationship which relates T1, T2, and $M_o$ to said induced signal is $$f_{ij} = M_o \{1 - (\exp(-\tau_i/T1))\} \exp(-2t_{cp} j/T2)$$

where $f_{ij}$ is said induced signal at the j'th echo after the i'th recovery time, and c is a constant relating to said borehole tool.

53. A method according to claim 52, wherein:

said step of determining a value for at least one of T1 and $M_o$ comprises conducting a non-linear least squares fit to find values for T1, T2, and $M_o$ which fit said induced signal measurements to said relationship.

54. A method according to claim 53, further comprising:

e) from said determination of at least one of T1 and $M_o$, determining one of the porosity and permeability of said formation according to a second relationship which relates one of T1 and $M_o$ to one of porosity and permeability.

55. A method according to claim 43, wherein said step of determining an indication of an attribute of said formation comprises determining either a spin-lattice relaxation time (T1k) of at least one component of said formation or an amplitude parameter ($M_{ok}$) from said measured induced signals according to a relationship which relates spin-lattice relaxation times and amplitudes to the magnitude of said induced signals, wherein the sum of $M_{ok}$'s is equal to the equilibrium value of the longitudinal magnetization 56. A method according to claim 43, wherein
said relationship relates T1k, T2k and $M_{ok}$, to said induced signal, according to $$f_{ij} = \sum_{k=1}^{n} M_{ok}\{1 - e^{-\tau_i/T1k}\}e^{-2t_{cpj}/T2k}$$

wherein k varies from one to at least two, T2k are the spin-spin relaxation times associated with respective components of said formation, the sum of $M_{ok}$ is proportional to the equilibrium value of the longitudinal magnetization, $f_{ij}$ is said induced signal at the j'th echo after the i'th recovery time, and c is a constant relating to said borehole tool.

57. A method according to claim 56, wherein:
said step of determining a value for at least T1k comprises conducting a non-linear least squares fit to find values for T1k, T2k, and $M_{ok}$ which fit said induced signal measurements to said relationship.

58. A method according to claim 57, further comprising:
e) from said determinations of at least one of T1k and $M_{ok}$, determining at least one of the porosity, permeability, and irreducible water saturation of said formation according to a second relationship which relates one of T1k and $M_{ok}$ to one of porosity, permeability, and irreducible water saturation.

59. A method according to claim 43, wherein:
said step of determining an indication of an attribute of said formation comprises determining at least a value for one of the stretch exponential spin-lattice relaxation time (T1α) of said formation and an amplitude $M_o$ parameter of said formation from said measured induced signals according to a relationship which relates said T1α and $M_o$ to the magnitude of said induced signals.

60. A method according to claim 59, wherein:
said relationship relates T1α, T2α, α1, α2, and $M_o$, to said induced signal, according to $$f_{ij} = M_o\{exp[-(2t_{cpj}/T2\alpha)^{\alpha 2}] - exp[-((\tau_i/T1\alpha) + (2t_{cpj}/T2\alpha))^{\alpha 1}]\}$$

wherein T2 is the stretched exponential spin-spin relaxation times associated with said formation, 1 and 2 are the stretch exponents, $M_o$ is proportional to the equilibrium value of the longitudinal magnetization, $f_{ij}$ is said induced signal at the j'th echo after the i'th recovery time, and c is a constant relating to said borehole tool.

61. A method according to claim 60, wherein:
said step of determining a value for at least T1α comprises conducting a non-linear least squares fit to find values for T1α, T2α, α1, α2, and $M_o$ which fit said induced signal measurements to said relationship.

62. A method according to claim 61, further comprising:
e) from said determination of at least one of T1α, and $M_o$, determining at least one of the porosity and permeability of said formation according to a second relationship which relates at least one of T1α, and $M_o$ to one of porosity and permeability.

* * * * *